US009290684B2

(12) United States Patent
Sherman et al.

(10) Patent No.: US 9,290,684 B2
(45) Date of Patent: *Mar. 22, 2016

(54) POLYDIORGANOSILOXANE POLYAMIDE COPOLYMERS HAVING ORGANIC SOFT SEGMENTS

(71) Applicant: 3M INNOVATIVE PROPERTIES COMPANY, St. Paul, MN (US)

(72) Inventors: Audrey A. Sherman, Woodbury, MN (US); Stephen A. Johnson, Woodbury, MN (US); Richard G. Hansen, Mahtomedi, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/665,243

(22) Filed: Mar. 23, 2015

(65) Prior Publication Data

US 2015/0197675 A1    Jul. 16, 2015

Related U.S. Application Data

(63) Continuation of application No. 14/095,328, filed on Dec. 3, 2013, now Pat. No. 9,018,331, which is a continuation of application No. 13/721,370, filed on Dec. 20, 2012, now Pat. No. 8,623,988, which is a continuation of application No. 13/253,620, filed on Oct. 5, 2011, now Pat. No. 8,361,626, which is a continuation of application No. 11/821,575, filed on Jun. 22, 2007, now Pat. No. 8,063,166.

(51) Int. Cl.
| *C08G 77/26* | (2006.01) |
| *C09J 183/12* | (2006.01) |
| *C08G 69/42* | (2006.01) |
| *C08G 77/455* | (2006.01) |
| *C08L 83/10* | (2006.01) |
| *C09J 183/10* | (2006.01) |
| *C08G 77/54* | (2006.01) |
| *C09J 183/08* | (2006.01) |

(52) U.S. Cl.
CPC ............... *C09J 183/12* (2013.01); *C08G 69/42* (2013.01); *C08G 77/455* (2013.01); *C08G 77/54* (2013.01); *C08L 83/10* (2013.01); *C09J 183/08* (2013.01); *C09J 183/10* (2013.01); *Y10T 428/1424* (2015.01); *Y10T 428/1462* (2015.01); *Y10T 428/31551* (2015.04); *Y10T 428/31663* (2015.04)

(58) Field of Classification Search
CPC ....... C08G 69/42; C08G 77/26; C08G 77/455
See application file for complete search history.

(56) References Cited

U.S. PATENT DOCUMENTS

| 2,532,011 A | 11/1950 | Dahlquist |
| 2,676,182 A | 4/1954 | Daudt |
| 2,736,721 A | 2/1956 | Dexter |
| 3,627,851 A | 12/1971 | Brady |
| 3,772,247 A | 11/1973 | Flannigan |
| 3,890,269 A | 6/1975 | Martin |
| 4,119,615 A | 10/1978 | Schulze |
| 4,661,577 A | 4/1987 | Jo Lane |
| 4,889,753 A | 12/1989 | Brown |
| 4,935,484 A | 6/1990 | Wolfgruber |
| 5,026,890 A | 6/1991 | Webb |
| 5,082,706 A | 1/1992 | Tangney |
| 5,091,483 A | 2/1992 | Mazurek |
| 5,110,890 A | 5/1992 | Butler |
| 5,214,119 A | 5/1993 | Leir |
| 5,248,739 A | 9/1993 | Schmidt |
| 5,276,122 A | 1/1994 | Aoki |
| 5,290,615 A | 3/1994 | Tushaus |
| 5,302,685 A | 4/1994 | Tsumura |
| 5,319,040 A | 6/1994 | Wengrovius |
| 5,461,134 A | 10/1995 | Leir |
| 5,512,650 A | 4/1996 | Leir |
| 5,539,033 A | 7/1996 | Bredahl |
| 5,663,262 A | 9/1997 | Shirakawa |
| 5,981,680 A | 11/1999 | Petroff |
| 6,051,216 A | 4/2000 | Barr |
| 6,355,759 B1 | 3/2002 | Sherman |
| 6,407,195 B2 | 6/2002 | Sherman |
| 6,441,118 B2 | 8/2002 | Sherman |
| 6,451,295 B1 | 9/2002 | Cai |
| 6,531,620 B2 | 3/2003 | Brader |
| 6,534,615 B2 | 3/2003 | Schafer |
| 6,664,359 B1 | 12/2003 | Kangas |
| 6,730,397 B2 | 5/2004 | Melancon |
| 6,846,893 B1 | 1/2005 | Sherman |

(Continued)

FOREIGN PATENT DOCUMENTS

| EP | 0311262 A2 | 4/1989 |
| EP | 0378420 | 7/1990 |

(Continued)

OTHER PUBLICATIONS

ASTM-D 1003-95, "Standard Test Method for Haze and Luminous Transmittance of Transparent Plastics," *Annual Book of ASTM Standards*, pp. 197-201(1995).

(Continued)

*Primary Examiner* — Kuo-Liang Peng

(74) *Attorney, Agent, or Firm* — Jeffrey M. Olofson

(57) ABSTRACT

Polydiorganosiloxane polyamide, block copolymers having organic soft segments and methods of making the copolymers are provided.

20 Claims, No Drawings

(56) References Cited

U.S. PATENT DOCUMENTS

| | | | |
|---|---|---|---|
| 7,026,424 B2 | 4/2006 | Schafer | |
| 7,153,924 B2 | 12/2006 | Keupfer | |
| 8,063,166 B2 * | 11/2011 | Sherman et al. | 528/38 |
| 8,361,626 B2 * | 1/2013 | Sherman et al. | 428/447 |
| 8,623,988 B2 * | 1/2014 | Sherman et al. | 528/38 |
| 9,018,331 B2 * | 4/2015 | Sherman et al. | 528/38 |
| 2003/0165676 A1 | 9/2003 | Zhou | |
| 2003/0175510 A1 | 9/2003 | Sherman | |
| 2003/0235553 A1 | 12/2003 | Lu | |
| 2004/0115153 A1 | 6/2004 | Yu | |
| 2004/0120912 A1 | 6/2004 | Yu | |
| 2005/0136266 A1 | 6/2005 | Zhou | |
| 2006/0194937 A1 | 8/2006 | Schafer | |
| 2007/0148474 A1 * | 6/2007 | Leir et al. | 428/447 |
| 2007/0148475 A1 | 6/2007 | Sherman | |
| 2007/0149745 A1 | 6/2007 | Leir | |
| 2007/0177272 A1 | 8/2007 | Benson | |
| 2007/0177273 A1 | 8/2007 | Benson | |

FOREIGN PATENT DOCUMENTS

| | | |
|---|---|---|
| EP | 0421643 | 4/1991 |
| EP | 0433070 A2 | 6/1991 |
| EP | 0311262 B1 | 12/1992 |
| EP | 0 589 440 | 3/1994 |
| EP | 0433070 B1 | 1/1996 |
| JP | HEI 2-36234 | 2/1990 |
| JP | 2002-036234 | 2/2002 |
| WO | WO 97-40103 | 10/1997 |
| WO | WO 2004-054523 | 7/2004 |

OTHER PUBLICATIONS

*Encyclopedia of Polymer Science and Engineering*, vol. 15, John Wiley & Sons, New York, (1989), pp. 265-270.

McGrath et al., "Synthesis and Characterization of Segmented Siloxane Copolymers," Polymer Preprints, vol. 39, No. 1, Mar. 1998, pp. 455-456.

Nielsen, et al., "Viscoelastic Damper Overview for Seismic and Wind Applications," Proceedings of SPIE—vol. 2720, Smart *Structures and Materials* 1996: *Passive Damping and Isolation*, Conor D. Johnson, Editor; May 1996; pp. 138-144.

U.S. Appl. No. 11/821,568, filed Jun. 22, 2007.
U.S. Appl. No. 11/821,571, filed Jun. 22, 2007.
U.S. Appl. No. 11/821,572, filed Jun. 22, 2007.
U.S. Appl. No. 11/821,596, filed Jun. 22, 2007.

* cited by examiner

POLYDIORGANOSILOXANE POLYMIDE COPOLYMERS HAVING ORGANIC SOFT SEGMENTS

TECHNICAL FIELD

Polydiorganosiloxane polyamide copolymers having organic soft segments and methods of making the copolymers are described.

BACKGROUND

Siloxane polymers have unique properties derived mainly from the physical and chemical characteristics of the siloxane bond. These properties include low glass transition temperature, thermal and oxidative stability, resistance to ultraviolet radiation, low surface energy and hydrophobicity, high permeability to many gases, and biocompatibility. The siloxane polymers, however, often lack tensile strength.

The low tensile strength of the siloxane polymers can be improved by forming block copolymers. Some block copolymers contain a "soft" siloxane polymeric block or segment and any of a variety of "hard" blocks or segments. Polydiorganosiloxane polyamides and polydiorganosiloxane polyureas are exemplary block copolymers.

Polydiorganosiloxane polyamides have been prepared by condensation reactions of amino terminated silicones with short-chained dicarboxylic acids. Alternatively, these copolymers have been prepared by condensation reactions of carboxy terminated silicones with short-chained diamines. Because polydiorganosiloxanes (e.g., polydimethylsiloxanes) and polyamides often have significantly different solubility parameters, it can be difficult to find reaction conditions for production of siloxane-based polyamides that result in high degrees of polymerization, particularly with larger homologs of the polyorganosiloxane segments. Many of the known siloxane-based polyamide copolymers contain relatively short segments of the polydiorganosiloxane (e.g., polydimethylsiloxane) such as segments having no greater than 30 diorganosiloxy (e.g., dimethylsiloxy) units or the amount of the polydiorganosiloxane segment in the copolymer is relatively low. That is, the fraction (i.e., amount based on weight) of polydiorganosiloxane (e.g., polydimethylsiloxane) soft segments in the resulting copolymers tends to be low.

Polydiorganosiloxane polyureas are another type of block copolymer. Although these block copolymers have many desirable characteristics, some of them tend to degrade when subjected to elevated temperatures such as 250° C. or higher.

SUMMARY

In one aspect, the present disclosure provides a copolymer including: at least one repeat unit of Formula I (I-a and/or I-b):

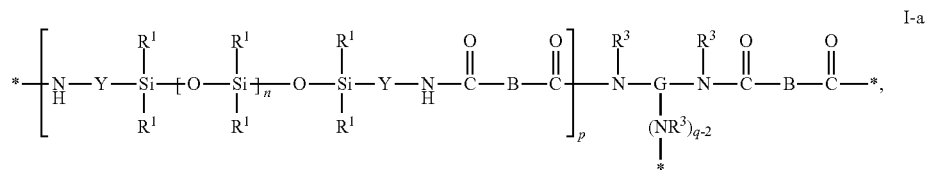

and at least one repeat unit of Formula VI (VI-a and/or VI-b):

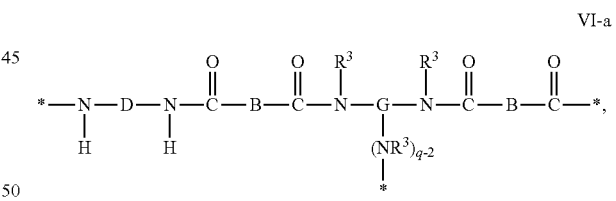

wherein: each $R^1$ is independently an alkyl, haloalkyl, aralkyl, alkenyl, aryl, or aryl substituted with an alkyl, alkoxy, or halo; G is a residue having a valence of q; $R^3$ is hydrogen or alkyl or $R^3$ taken together with G and to the nitrogen to which they are both attached form a heterocyclic group; each Y is independently an alkylene, aralkylene, or a combination thereof; each B is independently a covalent bond (e.g., a repeat unit of Formula I-b or Formula VI-b), an alkylene of 4-20 carbons, an aralkylene, an arylene, or a combination thereof; D is an organic soft segment residue; n is independently an integer of 0 to 1500; p is an integer of 1 to 10; and q is an integer greater than or equal to 2. Compositions and articles (e.g., films and/or composite films) including one or more copolymers having at least one repeat unit of Formula I (I-a and/or I-b) and at least one repeat unit of Formula VI (VI-a and/or VI-b) are also disclosed herein.

In another aspect, the present disclosure provides a method of making a copolymer having at least one repeat unit of Formula I (I-a and/or I-b) and at least one repeat unit of Formula VI (VI-a and/or VI-b). The method includes mixing together under reaction conditions: a) a precursor of Formula II (II-a and/or II-b):

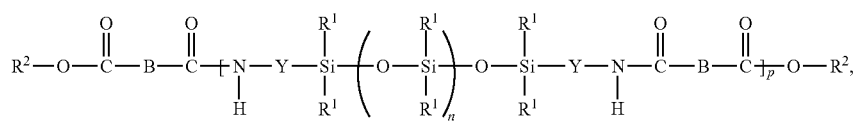

b) a precursor of Formula VII (VII-a and/or VII-b):

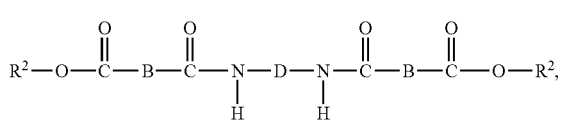

and c) one or more amine compounds having on average a formula $G(NHR^3)_r$, wherein: each $R^1$ is independently an alkyl, haloalkyl, aralkyl, alkenyl, aryl, or aryl substituted with an alkyl, alkoxy, or halo; each $R^2$ is independently an alkyl, haloalkyl, aryl, or aryl substituted with an alkyl, alkoxy, halo, or alkoxycarbonyl; G is a residue unit equal to the formula $G(NHR^3)_r$ minus the r —$NHR^3$ groups; $R^3$ is hydrogen or alkyl or $R^3$ taken together with G and with the nitrogen to which they are both attached forms a heterocyclic group; each Y is independently an alkylene, aralkylene, or a combination thereof; each B is independently a covalent bond (e.g., a precursor of Formula II-b or VII-b), an alkylene of 4-20 carbons, an aralkylene, an arylene, or a combination thereof; D is an organic soft segment residue; n is independently an integer of 0 to 1500; p is an integer of 1 to 10; and r is a number greater than or equal to 2.

In another aspect, the present disclosure provides a method of making a copolymer having at least one repeat unit of Formula I (I-a and/or I-b) and at least one repeat unit of Formula VI (VI-a and/or VI-b). The method includes mixing together under reaction conditions: a) a precursor of Formula VIII (VIII-a and/or VIII-b):

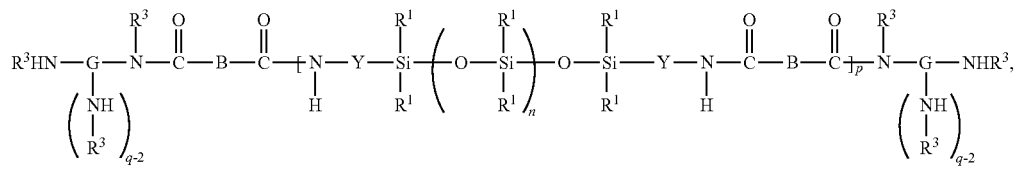

and
b) a precursor of Formula VII (VII-a and/or VII-b):

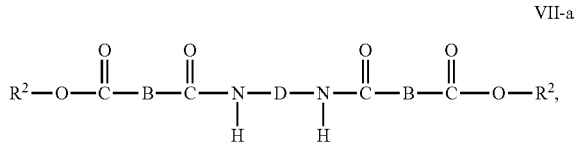

wherein: each $R^1$ is independently an alkyl, haloalkyl, aralkyl, alkenyl, aryl, or aryl substituted with an alkyl, alkoxy, or halo; each $R^2$ is independently an alkyl, haloalkyl, aryl, or aryl substituted with an alkyl, alkoxy, halo, or alkoxycarbonyl; G is a residue unit equal to the formula $G(NHR^3)_q$ minus the q —$NHR^3$ groups; $R^3$ is hydrogen or alkyl or $R^3$ taken together with G and with the nitrogen to which they are both attached forms a heterocyclic group; each Y is independently an alkylene, aralkylene, or a combination thereof; each B is independently a covalent bond (e.g., a precursor of Formula VIII-b or VII-b), an alkylene of 4-20 carbons, an aralkylene, an arylene, or a combination thereof; D is an organic soft segment residue; n is independently an integer of 0 to 1500; p is an integer of 1 to 10; and q is an integer greater than or equal to 2.

In certain embodiments, the present disclosure provides a process for producing a mixture, wherein the process includes: continuously providing at least one polydiorganosiloxane polyamide-containing component and at least one organic polymer to a vessel; mixing the components to form a mixture; and conveying the mixture from the vessel.

In certain embodiments, the mixing is under substantially solventless conditions.

In certain embodiments, the present disclosure provides a process for producing a mixture, wherein the process includes: continuously providing reactant components for making at least one polydiroganosiloxane polyamide and at least one organic polymer that is not reactive with the reactant components; mixing the components; allowing the reactant components to react to form a polydiorganosiloxane amide segmented copolymer, and conveying the mixture from the reactor.

The presently disclosed polydiorganosiloxane polyamide copolymers and methods of preparing such polymers can allow for "tuning" of surface and mechanical properties such as refractive index values, moisture transmission rates, release level, ink receptivity, water dispersability, adhesion, mechanical strength, permeability, and/or Tg, while maintaining sufficient thermal stability to allow the copolymer to be used, for example, in extrusion processes. The ability to "tune" such surface and mechanical properties can allow the polydiorganosiloxane polyamide copolymers to be used in a wide range of applications including, but not limited to, adhesives, pressure sensitive adhesives, extrudable resins, and skin layers. For example, when a polydiorganosiloxane polyamide copolymer is used as a low adhesion surface against a pressure sensitive adhesive, the release properties of the copolymer can be "tuned" by substituting some of the silicone soft segments with non-silicone soft segments (e.g., polyether segments).

The presently disclosed polydiorganosiloxane polyamide copolymers can be conceived for use in numerous applications including, for example, in sealants, adhesives, as material for fibers, as plastics additives, e.g., as impact modifiers or flame retardants, as material for defoamer formulations, as a high-performance polymer (thermoplastic, thermoplastic elastomer, elastomer), as packaging material for electronic components, in insulating materials or shielding materials, in cable sheathing, in antifouling materials, as an additive for scouring, cleaning, or polishing products, as an additive for bodycare compositions, as a coating material for wood, paper, and board, as a mold release agent, as a biocompatible material in medical applications such as contact lenses, as a coating material for textile fibers or textile fabric, as a coating material for natural substances such as leather and furs, for example, as a material for membranes and as a material for photoactive systems, for example, for lithographic techniques, optical data securement or optical data transmission.

DEFINITIONS

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "a", "an", and "the" are used interchangeably with "at least one" to mean one or more of the elements being described.

As used herein, the term "or" is generally employed in its sense including "and/or" unless the content clearly dictates otherwise.

The term "and/or" means one or all of the listed elements or a combination of any two or more of the listed elements.

The term "alkenyl" refers to a monovalent group that is a radical of an alkene, which is a hydrocarbon with at least one carbon-carbon double bond. The alkenyl can be linear, branched, cyclic, or combinations thereof and typically contains 2 to 20 carbon atoms. In some embodiments, the alkenyl contains 2 to 18, 2 to 12, 2 to 10, 4 to 10, 4 to 8, 2 to 8, 2 to 6, or 2 to 4 carbon atoms. Exemplary alkenyl groups include ethenyl, n-propenyl, and n-butenyl.

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

The term "alkylene" refers to a divalent group that is a radical of an alkane. The alkylene can be straight-chained, branched, cyclic, or combinations thereof. The alkylene often has 1 to 20 carbon atoms. In some embodiments, the alkylene contains 1 to 18, 1 to 12, 1 to 10, 1 to 8, 1 to 6, or 1 to 4 carbon atoms. The radical centers of the alkylene can be on the same carbon atom (i.e., an alkylidene) or on different carbon atoms.

The term "alkoxy" refers to a monovalent group of formula —OR where R is an alkyl group.

The term "alkoxycarbonyl" refers to a monovalent group of formula —(CO)OR where R is an alkyl group and (CO) denotes a carbonyl group with the carbon attached to the oxygen with a double bond.

The term "aralkyl" refers to a monovalent group of formula —$R^a$—Ar where $R^a$ is an alkylene and Ar is an aryl group. That is, the aralkyl is an alkyl substituted with an aryl.

The term "aralkylene" refers to a divalent group of formula —$R^a$—$Ar^a$— where $R^a$ is an alkylene and $Ar^a$ is an arylene (i.e., an alkylene is bonded to an arylene).

The term "aryl" refers to a monovalent group that is aromatic and carbocyclic. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

The term "arylene" refers to a divalent group that is carbocyclic and aromatic. The group has one to five rings that are connected, fused, or combinations thereof. The other rings can be aromatic, non-aromatic, or combinations thereof. In some embodiments, the arylene group has up to 5 rings, up to 4 rings, up to 3 rings, up to 2 rings, or one aromatic ring. For example, the arylene group can be phenylene.

The term "aryloxy" refers to a monovalent group of formula —OAr where Ar is an aryl group.

The term "carbonyl" refers to a divalent group of formula —(CO)— where the carbon atom is attached to the oxygen atom with a double bond.

The term "halo" refers to fluoro, chloro, bromo, or iodo.

The term "haloalkyl" refers to an alkyl having at least one hydrogen atom replaced with a halo. Some haloalkyl groups are fluoroalkyl groups, chloroalkyl groups, or bromoalkyl groups.

The term "heteroalkylene" refers to a divalent group that includes at least two alkylene groups connected by a thio, oxy, or —NR— where R is alkyl. The heteroalkylene can be linear, branched, cyclic, or combinations thereof and can include up to 60 carbon atoms and up to 15 heteroatoms. In some embodiments, the heteroalkylene includes up to 50 carbon atoms, up to 40 carbon atoms, up to 30 carbon atoms, up to 20 carbon atoms, or up to 10 carbon atoms. Some heteroalkylenes are polyalkylene oxides where the heteroatom is oxygen.

The term "oxalyl" refers to a divalent group of formula —(CO)—(CO)— where each (CO) denotes a carbonyl group.

The terms "oxalylamino" and "aminoxalyl" are used interchangeably to refer to a divalent group of formula —(CO)—(CO)—NH— where each (CO) denotes a carbonyl.

The term "aminoxalylamino" refers to a divalent group of formula —NH—(CO)—(CO)—$NR^d$— where each (CO) denotes a carbonyl group and $R^d$ is hydrogen, alkyl, or part of a heterocyclic group along with the nitrogen to which they are both attached. In most embodiments, $R^d$ is hydrogen or alkyl. In many embodiments, $R^d$ is hydrogen.

The term "polyvalent" refers to a group having a valence of greater than 2.

The terms "polymer" and "polymeric material" refer to both materials prepared from one monomer such as a homopolymer or to materials prepared from two or more monomers such as a copolymer, terpolymer, or the like. Likewise, the term "polymerize" refers to the process of making a polymeric material that can be a homopolymer, copolymer, terpolymer, or the like. The terms "copolymer" and "copolymeric material" refer to a polymeric material prepared from at least two monomers.

The term "polydiorganosiloxane" refers to a divalent segment of formula

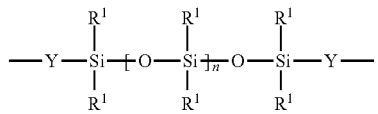

where each $R^1$ is independently an alkyl, haloalkyl, aralkyl, alkenyl, aryl, or aryl substituted with an alkyl, alkoxy, or halo; each Y is independently an alkylene, aralkylene, or a combination thereof; and subscript n is independently an integer of 0 to 1500.

The terms "room temperature" and "ambient temperature" are used interchangeably to mean temperatures in the range of 20° C. to 25° C.

Unless otherwise indicated, all numbers expressing feature sizes, amounts, and physical properties used in the specification and claims are to be understood as being modified in all instances by the term "about." Accordingly, unless indicated to the contrary, the numbers set forth are approximations that can vary depending upon the desired properties using the teachings disclosed herein.

The above summary of the present invention is not intended to describe each disclosed embodiment or every implementation of the present invention. The description that follows more particularly exemplifies illustrative embodiments. In several places throughout the application, guidance is provided through lists of examples, which can be used in various combinations. In each instance, the recited list serves only as a representative group and should not be interpreted as an exclusive list.

DETAILED DESCRIPTION OF ILLUSTRATIVE EMBODIMENTS

Polydiorganosiloxane polyamide block copolymers having amide end-capped (e.g., oxalated) organic soft segments and methods of making the copolymers are disclosed herein. In certain embodiments, the block copolymers are polydiorganosiloxane polyoxamide block copolymers having amide end-capped (e.g., oxalated) organic soft segments. The polydiorganosiloxane polyamide copolymers can be linear or branched. As used herein, the term "branched" is used to refer to a polymer chain having branch points that connect three or more chain segments. Examples of branched polymers include long chains having occasional and usually short branches including the same repeat units as the main chain (nominally termed a branched polymer). Branched polydiorganosiloxane polyamide block copolymers having amide end-capped organic soft segments can optionally form cross-linked networks.

The copolymers can have many of the desirable features of polysiloxanes such as low glass transition temperatures, thermal and oxidative stability, resistance to ultraviolet radiation, low surface energy and hydrophobicity, and high permeability to many gases. Additionally, the copolymers can have improved mechanical strength and elastomeric properties compared to polysiloxanes and linear polydiorganosiloxane polyamide block copolymers. At least some of the copolymers are optically clear, have a low refractive index, or both.

Polydiorganosiloxane Polyamide Block Copolymers Having Amide End-Capped Organic Soft Segments A polydiorganosiloxane polyamide block copolymer is provided that contains at least one repeat unit of Formula I-a:

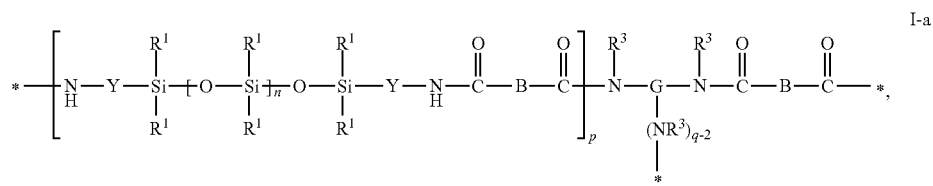

and at least one repeat unit of Formula VI-a:

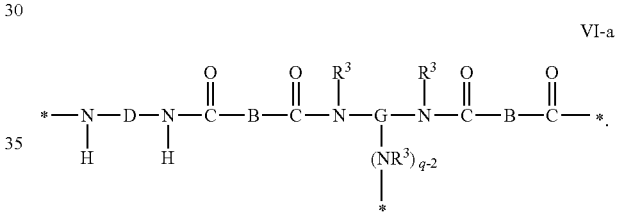

In these formulas, each $R^1$ is independently an alkyl, haloalkyl, aralkyl, alkenyl, aryl, or aryl substituted with an alkyl, alkoxy, or halo. G is a residue unit equal to the formula $G(NHR^3)_q$ minus the q —$NHR^3$ groups, and q is an integer greater than or equal to 2. In certain embodiments q can, for example, be equal to 2, 3, or 4. Group $R^3$ is hydrogen or alkyl (e.g., an alkyl having 1 to 10, 1 to 6, or 1 to 4 carbon atoms) or $R^3$ taken together with G and with the nitrogen to which they are both attached forms a heterocyclic group (e.g., $R^3HN$-G-$NHR^3$ is piperazine or the like). Each Y is independently an alkylene, aralkylene, or a combination thereof. Subscript n is independently an integer of 0 to 1500 and the subscript p is an integer of 1 to 10. D is an organic soft segment residue. Each B is independently a covalent bond, an alkylene of 4-20 carbons, an aralkylene, an arylene, or a combination thereof. When each group B is a covalent bond, the polydiorganosiloxane polyamide block copolymer having repeat units of Formulas I-a and VI-a is referred to as a polydiorganosiloxane polyoxamide block copolymer, and preferably has repeat unit of Formulas I-b and VI-b as shown below. Each asterisk (*) indicates a site of attachment of the repeat unit to another group in the copolymer such as, for example, another repeat unit of Formula I (I-a or I-b) or Formula VI (VI-a or VI-b).

A preferred polydiorganosiloxane polyoxamide block copolymer contains at least one repeat unit of Formula I-b:

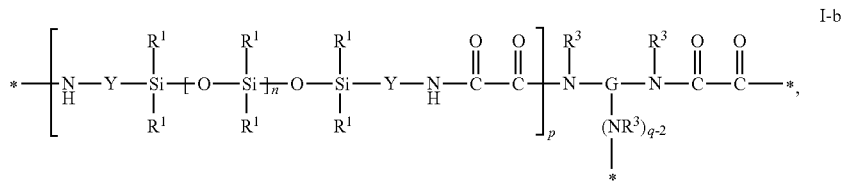

and
at least one repeat unit of Formula VI-b:

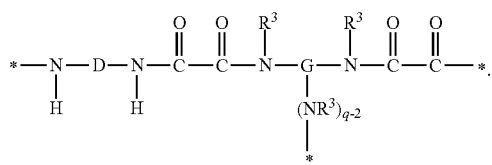

In this formula, each $R^1$ is independently an alkyl, haloalkyl, aralkyl, alkenyl, aryl, or aryl substituted with an alkyl, alkoxy, or halo. G is a residue unit equal to the formula $G(NHR^3)_q$ minus the q —$NHR^3$ groups, and q is an integer greater than or equal to 2. In certain embodiments q can, for example, be equal to 2, 3, or 4. Group $R^3$ is hydrogen or alkyl (e.g., an alkyl having 1 to 10, 1 to 6, or 1 to 4 carbon atoms) or $R^3$ taken together with G and with the nitrogen to which they are both attached forms a heterocyclic group (e.g., $R^3HN$-G-$NHR^3$ is piperazine or the like). Each Y is independently an alkylene, aralkylene, or a combination thereof. D is an organic soft segment residue. Subscript n is independently an integer of 0 to 1500 and the subscript p is an integer of 1 to 10. Each asterisk (*) indicates a site of attachment of the repeat unit to another group in the copolymer such as, for example, another repeat unit of Formula I (I-a or I-b) and/or Formula VI (VI-a or VI-b).

Suitable alkyl groups for $R^1$ in Formula I (I-a or I-b) typically have 1 to 10, 1 to 6, or 1 to 4 carbon atoms. Exemplary alkyl groups include, but are not limited to, methyl, ethyl, isopropyl, n-propyl, n-butyl, and iso-butyl. Suitable haloalkyl groups for $R^1$ often have only a portion of the hydrogen atoms of the corresponding alkyl group replaced with a halogen. Exemplary haloalkyl groups include chloroalkyl and fluoroalkyl groups with 1 to 3 halo atoms and 3 to 10 carbon atoms. Suitable alkenyl groups for $R^1$ often have 2 to 10 carbon atoms. Exemplary alkenyl groups often have 2 to 8, 2 to 6, or 2 to 4 carbon atoms such as ethenyl, n-propenyl, and n-butenyl. Suitable aryl groups for $R^1$ often have 6 to 12 carbon atoms. Phenyl is an exemplary aryl group. The aryl group can be unsubstituted or substituted with an alkyl (e.g., an alkyl having 1 to 10 carbon atoms, 1 to 6 carbon atoms, or 1 to 4 carbon atoms), an alkoxy (e.g., an alkoxy having 1 to 10 carbon atoms, 1 to 6 carbon atoms, or 1 to 4 carbon atoms), or halo (e.g., chloro, bromo, or fluoro). Suitable aralkyl groups for $R^1$ usually have an alkylene group with 1 to 10 carbon atoms and an aryl group with 6 to 12 carbon atoms. In some exemplary aralkyl groups, the aryl group is phenyl and the alkylene group has 1 to 10 carbon atoms, 1 to 6 carbon atoms, or 1 to 4 carbon atoms (i.e., the structure of the aralkyl is alkylene-phenyl where an alkylene is bonded to a phenyl group).

In some repeat units of Formula I (I-a or I-b), all $R^1$ groups can be one of alkyl, haloalkyl, aralkyl, alkenyl, aryl, or aryl substituted with an alkyl, alkoxy, or halo (e.g., all $R^1$ Groups are an alkyl such as methyl or an aryl such as phenyl). In some compounds of Formula II, the $R^1$ groups are mixtures of two or more selected from the group consisting of alkyl, haloalkyl, aralkyl, alkenyl, aryl, and aryl substituted with an alkyl, alkoxy, or halo in any ratio. Thus, for example, in certain compounds of Formula I, 0%, 1%, 2, %, 5%, 10%, 20%, 30%, 40%, 50%, 60%, 70%, 80%, 90%, 95%, 98%, 99%, or 100% of the $R^1$ groups can be methyl; and 100%, 99%, 98%, 95%, 90%, 80%, 70%, 60%, 50%, 40%, 30%, 20%, 10%, 5%, 2%, 1%, or 0% of the $R^1$ groups can be phenyl.

In some repeat units of Formula I (I-a or I-b), at least 50 percent of the $R^1$ groups are methyl. For example, at least 60 percent, at least 70 percent, at least 80 percent, at least 90 percent, at least 95 percent, at least 98 percent, or at least 99 percent of the $R^1$ groups can be methyl. The remaining $R^1$ groups can be selected from an alkyl having at least two carbon atoms, haloalkyl, aralkyl, alkenyl, aryl, or aryl substituted with an alkyl, alkoxy, or halo.

Each Y in Formula I (I-a or I-b) is independently an alkylene, aralkylene, or a combination thereof. Suitable alkylene groups typically have up to 10 carbon atoms, up to 8 carbon atoms, up to 6 carbon atoms, or up to 4 carbon atoms. Exemplary alkylene groups include methylene, ethylene, propylene, butylene, and the like. Suitable aralkylene groups usually have an arylene group with 6 to 12 carbon atoms bonded to an alkylene group with 1 to 10 carbon atoms. In some exemplary aralkylene groups, the arylene portion is phenylene. That is, the divalent aralkylene group is phenylene-alkylene where the phenylene is bonded to an alkylene having 1 to 10, 1 to 8, 1 to 6, or 1 to 4 carbon atoms. As used herein with reference to group Y, "a combination thereof" refers to a combination of two or more groups selected from an alkylene and aralkylene group. A combination can be, for example, a single aralkylene bonded to a single alkylene (e.g., alkylene-arylene-alkylene). In one exemplary alkylene-arylene-alkylene combination, the arylene is phenylene and each alkylene has 1 to 10, 1 to 6, or 1 to 4 carbon atoms.

Each subscript n in Formula I (I-a or I-b) is independently an integer of 0 to 1500. For example, subscript n can be an integer up to 1000, up to 500, up to 400, up to 300, up to 200, up to 100, up to 80, up to 60, up to 40, up to 20, or up to 10. The value of n is often at least 1, at least 2, at least 3, at least 5, at least 10, at least 20, or at least 40. For example, subscript n can be in the range of 40 to 1500, 0 to 1000, 40 to 1000, 0 to 500, 1 to 500, 40 to 500, 1 to 400, 1 to 300, 1 to 200, 1 to 100, 1 to 80, 1 to 40, or 1 to 20.

The subscript p is an integer of 1 to 10. For example, the value of p is often an integer up to 9, up to 8, up to 7, up to 6, up to 5, up to 4, up to 3, or up to 2. The value of p can be in the range of 1 to 8, 1 to 6, or 1 to 4.

Group G in Formula I (I-a or I-b) and/or Formula VI (VI-a or VI-b) is a residual unit that is equal to a diamine or polyamine compound of formula $G(NHR^3)_q$ minus the q amino groups (i.e., —$NHR^3$ groups), where q is an integer greater than or equal to 2. The diamine and/or polyamine can have primary and/or secondary amino groups. Group $R^3$ is hydrogen or alkyl (e.g., an alkyl having 1 to 10, 1 to 6, or 1 to 4 carbon atoms) or $R^3$ taken together with G and with the nitrogen to which they are both attached forms a heterocyclic group (e.g., $R^3$HN-G-$NHR^3$ is piperazine). In most embodiments, $R^3$ is hydrogen or an alkyl. In many embodiments, all of the amino groups of the diamine and/or polyamine are primary amino groups (i.e., all the $R^3$ groups are hydrogen) and the diamine and/or polyamine are of the formula $G(NH_2)_q$ (e.g., a diamine of the formula $R^3$HN-G-$NHR^3$ when q=2).

In certain embodiments, Group G in Formula I (I-a or I-b) and/or Formula VI (VI-a or VI-b) is a mixture of residual units that are equal to (i) a diamine compound of the formula $R^3$HN-G-$NHR^3$ minus the two amino groups (i.e., —$NHR^3$ groups) and (ii) a polyamine compound of the formula $G(NHR^3)_q$ minus the q amino groups (i.e., —$NHR^3$ groups), where q is an integer greater than 2. In such embodiments, the polyamine compound of formula $G(NHR^3)_q$ can be, but is not limited to, triamine compounds (i.e., q=3), tetraamine compounds (i.e., q=4), and combinations thereof. In such embodiments, the number of equivalents of polyamine (ii) per equivalent of diamine (i) is preferably at least 0.001, more preferably at least 0.005, and most preferably at least 0.01. In such embodiments, the number of equivalents of polyamine (ii) per equivalent of diamine (i) is preferably at most 3, more preferably at most 2, and most preferably at most 1.

When G includes residual units that are equal to (i) a diamine compound of formula $R^3$HN-G-$NHR^3$ minus the two amino groups (i.e., —$NHR^3$ groups), G can be an alkylene, heteroalkylene, polydiorganosiloxane, arylene, aralkylene, or a combination thereof. Suitable alkylenes often have 2 to 10, 2 to 6, or 2 to 4 carbon atoms. Exemplary alkylene groups include ethylene, propylene, butylene, and the like. Suitable heteroalkylenes are often polyoxyalkylenes such as polyoxyethylene having at least 2 ethylene units, polyoxypropylene having at least 2 propylene units, or copolymers thereof. Suitable polydiorganosiloxanes include the polydiorganosiloxane diamines of Formula III, which are described below, minus the two amino groups. Exemplary polydiorganosiloxanes include, but are not limited to, polydimethylsiloxanes with alkylene Y groups. Suitable aralkylene groups usually contain an arylene group having 6 to 12 carbon atoms bonded to an alkylene group having 1 to 10 carbon atoms. Some exemplary aralkylene groups are phenylene-alkylene where the phenylene is bonded to an alkylene having 1 to 10 carbon atoms, 1 to 8 carbon atoms, 1 to 6 carbon atoms, or 1 to 4 carbon atoms. As used herein with reference to group G, "a combination thereof" refers to a combination of two or more groups selected from an alkylene, heteroalkylene, polydiorganosiloxane, arylene, and aralkylene. A combination can be, for example, an aralkylene bonded to an alkylene (e.g., alkylene-arylene-alkylene). In one exemplary alkylene-arylene-alkylene combination, the arylene is phenylene and each alkylene has 1 to 10, 1 to 6, or 1 to 4 carbon atoms.

Each D is Formula VI (VI-a or VI-b) represents an organic soft segment. Organic soft segments typically include one or more polyether residues such as, for example, polyoxyethylene residues, polyoxypropylene residues, poly(oxyethylene-co-oxypropylene) residues, and combinations thereof. The organic soft segment preferably has an average molecular weight of at least 450, more preferably at least 700, and most preferably at least 2000. The organic soft segment preferably has an average molecular weight of at most 8000, more preferably at most 6000, and most preferably at most 4000. A wide variety of organic soft segments can be used including, for example, those described in U.S. Pat. No. 4,119,615 (Schulze).

In preferred embodiments, the polydiorganosiloxane polyamide having amide end-capped (e.g., oxalated) organic soft segments is a polydiorganosiloxane polyoxamide. The polydiorganosiloxane polyamide tends to be free of groups having a formula —$R^a$—(CO)—NH— where $R^a$ is an alkylene. All of the carbonylamino groups along the backbone of the copolymeric material are part of an oxalylamino group (i.e., the —(CO)—(CO)—NH— group). That is, any carbonyl group along the backbone of the copolymeric material is bonded to another carbonyl group and is part of an oxalyl group. More specifically, the polydiorganosiloxane polyoxamide has a plurality of aminoxalylamino groups.

The polydiorganosiloxane polyamide having amide end-capped (e.g., oxalated) organic soft segments is a block copolymer and can be an elastomeric material. Unlike many of the known polydiorganosiloxane polyamides that are generally formulated as brittle solids or hard plastics, the polydiorganosiloxane polyamides can be formulated to include greater than 50 weight percent polydiorganosiloxane segments based on the weight of the copolymer. The weight percent of the diorganosiloxane in the polydiorganosiloxane polyamides can be increased by using higher molecular weight polydiorganosiloxanes segments to provide greater than 60 weight percent, greater than 70 weight percent, greater than 80 weight percent, greater than 90 weight percent, greater than 95 weight percent, or greater than 98 weight percent of the polydiorganosiloxane segments in the polydiorganosiloxane polyamides. Higher amounts of the polydiorganosiloxane can be used to prepare elastomeric materials with lower modulus while maintaining reasonable strength.

Some of the polydiorganosiloxane polyamides can be heated to a temperature up to 200° C., up to 225° C., up to 250° C., up to 275° C., or up to 300° C. without noticeable degradation of the material. For example, when heated in a thermogravimetric analyzer in the presence of air, the copolymers often have less than a 10 percent weight loss when scanned at a rate 50° C. per minute in the range of 20° C. to 350° C. Additionally, the copolymers can often be heated at a temperature such as 250° C. for 1 hour in air without apparent degradation as determined by no detectable loss of mechanical strength upon cooling.

The copolymeric material having repeat units of Formula I (I-a or I-b) and Formula VI (VI-a or VI-b) can be optically clear. As used herein, the term "optically clear" refers to a material that is clear to the human eye. An optically clear copolymeric material often has a luminous transmission of at least 90 percent, a haze of less than 2 percent, and opacity of less than 1 percent in the 400 to 700 nm wavelength range. Both the luminous transmission and the haze can be determined using, for example, the method of ASTM-D 1003-95.

Additionally, the copolymeric material having repeat units of Formula I (I-a or I-b) and Formula VI (VI-a or VI-b) can have a low refractive index. As used herein, the term "refractive index" refers to the absolute refractive index of a material (e.g., copolymeric material) and is the ratio of the speed of electromagnetic radiation in free space to the speed of the electromagnetic radiation in the material of interest. The electromagnetic radiation is white light. The index of refraction is measured using an Abbe refractometer, available commercially, for example, from Fisher Instruments of Pittsburgh, Pa. The measurement of the refractive index can depend, to some extent, on the particular refractometer used. For some embodiments (e.g., embodiments in which the copolymer includes a polydimethylsiloxane segment), the copolymeric material can have a refractive index in the range of 1.41 to 1.50. For some other embodiments (e.g., embodiments in which the copolymer includes a polyphenylsiloxane or a polydiphenylsiloxane segment), the copolymeric material can have a refractive index in the range of from 1.46 to 1.55.

Methods of Making Polydiorganosiloxane Polyamide Copolymers

Exemplary Method A-1

In one embodiment, the block copolymers having repeat units of Formula I-a and Formula VI-a can be prepared, for example, as follows. The method includes mixing together under reaction conditions: a) a precursor of Formula II-a:

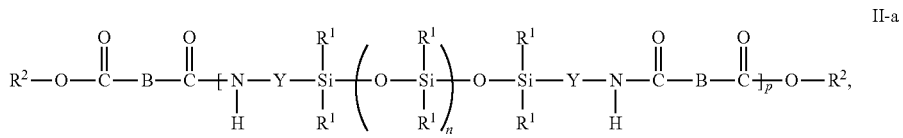

b) a precursor of Formula VII-a:

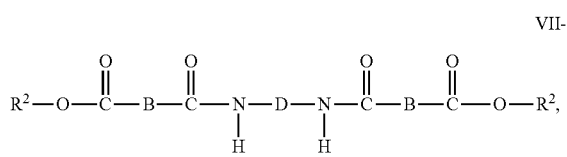

and c) one or more amine compounds having on average a formula $G(NHR^3)_r$.

Exemplary Method A-2

In another embodiment, the block copolymers having repeat units of Formula I-b and Formula VI-b can be prepared, for example, as follows. The method includes mixing together under reaction conditions: a) a precursor of Formula II-b:

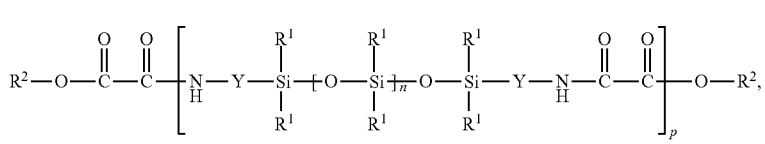

b) a precursor of Formula VII-b:

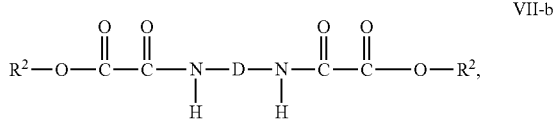

and c) one or more amine compounds having on average a formula $G(NHR^3)_r$.

In Exemplary Method A (A-1 and A-2), a precursor of Formula II (II-a or II-b), a precursor of Formula VII (VII-a and VII-b), and one or more amine compounds having on average r amino groups (e.g., primary and/or secondary amino groups) are combined under reaction conditions.

The one or more amine compounds are typically of the formula $G(NHR^3)_r$, where r on average is greater than or equal to 2. Group $R^3$ is hydrogen or alkyl (e.g., an alkyl having 1 to 10, 1 to 6, or 1 to 4 carbon atoms) or $R^3$ taken together with G and with the nitrogen to which they are both attached forms a heterocyclic group (e.g., $R^3HN\text{-}G\text{-}NHR^3$ is piperazine). In most embodiments, $R^3$ is hydrogen or an alkyl. In many embodiments, all of the amino groups of the one or more amine compounds are primary amino groups (i.e., all the $R^3$ groups are hydrogen) and the one or more amine compounds are of the formula $G(NH_2)_q$ (e.g., a diamine of the formula $R^3HN\text{-}G\text{-}NHR^3$ when q=2). The $R^2OH$ by-product is typically removed from the resulting polydiorganosiloxane polyamide.

In certain embodiments, the one or more amine compounds are a mixture of (i) a diamine compound of formula $R^3HN\text{-}G\text{-}NHR^3$ and (ii) a polyamine compound of formula $G(NHR^3)_q$, where q is an integer greater than 2. In such embodiments, the polyamine compound of formula $G(NHR^3)_q$ can be, but is not limited to, triamine compounds (i.e., q=3), tetraamine compounds (i.e., q=4), and combinations thereof. In such embodiments, the number of equivalents of polyamine (ii) per equivalent of diamine (i) is preferably at least 0.001, more preferably at least 0.005, and most preferably at least 0.01. In such embodiments, the number of equivalents of polyamine (ii) per equivalent of diamine (i) is preferably at most 3, more preferably at most 2, and most preferably at most 1.

Exemplary triamines include, but are not limited to, tris(2-aminoethyl)amine, diethylentriamine, polyoxyalkylene triamines such as those available, for example, from Huntsman (The Woodlands, Tex.) under the trade designations JEFFAMINE T-3000 (i.e., polyoxypropylene triamine having an average molecular weight of 3000 g/mole) and JEFFAMINE T-5000 (i.e., polyoxypropylene triamine having an average molecular weight of 5000 g/mole), amino-functional polysiloxanes, and combinations thereof. Exemplary tetraamines include, but are not limited to, triethylene tetraamine. Exemplary polydimethylsiloxanes having amino functionality include, for example, polydimethylsiloxane copolymers having aminopropylmethylsiloxane units such as those available under the trade designations AMS-132, AMS-152, and AMS-162 from Gelest, Inc., Morrisville, Pa.

When the one or more amine compounds include diamines, the diamines are sometimes classified as organic diamines or polydiorganosiloxane diamines with the organic diamines including, for example, those selected from alkylene diamines, heteroalkylene diamines, arylene diamines, aralkylene diamines, or alkylene-aralkylene diamines. Tertiary amines that do not react with the precursor of Formula II (II-a or II-b) can be present. Additionally, the diamine is free of any carbonylamino group. That is, the diamine is not an amide.

Exemplary polyoxyalkylene diamines (i.e., G is a heteroalkylene with the heteroatom being oxygen) include, but are not limited to, those commercially available from Huntsman, The Woodlands, Tex. under the trade designation JEFFAMINE D-230 (i.e., polyoxypropylene diamine having an average molecular weight of 230 g/mole), JEFFAMINE D-400 (i.e., polyoxypropylene diamine having an average molecular weight of 400 g/mole), JEFFAMINE D-2000 (i.e., polyoxypropylene diamine having an average molecular weight of 2,000 g/mole), JEFFAMINE HK-511 (i.e., polyetherdiamine with both oxyethylene and oxypropylene groups and having an average molecular weight of 220 g/mole), JEFFAMINE ED-2003 (i.e., polypropylene oxide capped polyethylene glycol having an average molecular weight of 2,000 g/mole), and JEFFAMINE EDR-148 (i.e., triethyleneglycol diamine).

Exemplary alkylene diamines (i.e., G is a alkylene) include, but are not limited to, ethylene diamine, propylene diamine, butylene diamine, hexamethylene diamine, 2-methylpentamethylene 1,5-diamine (i.e., commercially available from DuPont, Wilmington, Del. under the trade designation DYTEK A), 1,3-pentane diamine (commercially available from DuPont under the trade designation DYTEK EP), 1,4-cyclohexane diamine, 1,2-cyclohexane diamine (commercially available from DuPont under the trade designation DHC-99), 4,4'-bis(aminocyclohexyl)methane, and 3-aminomethyl-3,5,5-trimethylcyclohexylamine.

Exemplary arylene diamines (i.e., G is an arylene such as phenylene) include, but are not limited to, m-phenylene diamine, o-phenylene diamine, and p-phenylene diamine. Exemplary aralkylene diamines (i.e., G is an aralkylene such as alkylene-phenyl) include, but are not limited to 4-aminomethyl-phenylamine, 3-aminomethyl-phenylamine, and 2-aminomethyl-phenylamine. Exemplary alkylene-aralkylene diamines (i.e., G is an alkylene-aralkylene such as alkylene-phenylene-alkylene) include, but are not limited to, 4-aminomethyl-benzylamine, 3-aminomethyl-benzylamine, and 2-aminomethyl-benzylamine.

The precursor of Formulas II-a and II-b, respectively, have at least one polydiorganosiloxane segment and at least two amido groups (e.g., oxalylamino groups). Group $R^1$, group Y, subscript n, and subscript p are the same as described for Formula I (I-a or I-b). Each group $R^2$ is independently an alkyl, haloalkyl, aryl, or aryl substituted with an alkyl, alkoxy, halo, or alkoxycarbonyl. The precursor of Formula II (II-a or II-b) can include a single compound (i.e., all the compounds have the same value of p and n) or can include a plurality of compounds (i.e., the compounds have different values for p, different values for n, or different values for both p and n). Precursors with different n values have siloxane chains of different length. Precursors having a p value of at least 2 are chain extended.

In some embodiments, the precursor is a mixture of a first compound of Formula II (II-a and/or II-b) with subscript p equal to 1 and a second compound of Formula II (II-a and/or II-b) with subscript p equal to at least 2. The first compound can include a plurality of different compounds with different values of n. The second compound can include a plurality of compounds with different values of p, different values of n, or different values of both p and n. Mixtures can include at least 50 weight percent of the first compound of Formula II (II-a or II-b) (i.e., p is equal to 1) and no greater than 50 weight percent of the second compound of Formula II (II-a or II-b) (i.e., p is equal to at least 2) based on the sum of the weight of the first and second compounds in the mixture. In some mixtures, the first compound is present in an amount of at least 55 weight percent, at least 60 weight percent, at least 65 weight percent, at least 70 weight percent, at least 75 weight percent, at least 80 weight percent, at least 85 weight percent, at least 90 weight percent, at least 95 weight percent, or at least 98 weight percent based on the total amount of the compounds of Formula II. The mixtures often contain no greater than 50 weight percent, no greater than 45 weight percent, no greater than 40 weight percent, no greater than 35 weight percent, no greater than 30 weight percent, no greater than 25 weight percent, no greater than 20 weight percent, no greater than 15 weight percent, no greater than 10 weight percent, no greater than 5 weight percent, or no greater than 2 weight percent of the second compound.

Different amounts of the chain-extended precursor of Formula II (II-a or II-b) in the mixture can affect the final properties of the elastomeric material having repeat units of Formula I (I-a or I-b). That is, the amount of the second compound of Formula II (II-a or II-b) (i.e., p equal to at least 2) can be varied advantageously to provide elastomeric materials with a range of properties. For example, a higher amount of the second compound of Formula II (II-a or II-b) can alter the melt rheology (e.g., the elastomeric material can flow easier when present as a melt), alter the softness of the elastomeric material, lower the modulus of the elastomeric material, or a combination thereof.

Precursors of Formula VII (VII-a and VII-b) methods known in the art. In some embodiments an amine terminated organic soft segment (e.g., $H_2N-D-NH_2$) can be end-capped with an appropriate reagent to yield precursors of Formula VII (VII-a and VII-b). For example, an amine terminated organic soft segment (e.g., $H_2N-D-NH_2$) can be end-capped with oxalic acid and/or an oxalic acid ester to form a precursor of Formula VII-b as described, for example, in U.S. Pat. No. 4,119,615 (Schulze).

Amine terminated organic soft segments can be represented, for example, by the formula $H_2N-D-NH_2$, wherein D represents an organic soft segment. Organic soft segments typically include one or more polyether residues such as, for example, polyoxyethylene residues, polyoxypropylene residues, poly(oxyethylene-co-oxypropylene) residues, and combinations thereof. The organic soft segment preferably has an average molecular weight of at least 450, more preferably at least 700, and most preferably at least 2000. The organic soft segment preferably has an average molecular weight of at most 8000, more preferably at most 6000, and most preferably at most 4000. A wide variety of amine terminated organic soft segments can be useful including, for example, polyoxyalkylene diamines, polyoxyalkylene triamines, and those described, for example, in U.S. Pat. No. 4,119,615 (Schulze).

Exemplary polyoxyalkylene diamines include, but are not limited to, those available from Huntsman, The Woodlands, Tex. under the trade designation JEFFAMINE D-230 (i.e., polyoxypropylene diamine having an average molecular weight of 230 g/mole), JEFFAMINE D-400 (i.e., polyoxypropylene diamine having an average molecular weight of 400 g/mole), JEFFAMINE D-2000 (i.e., polyoxypropylene diamine having an average molecular weight of 2,000 g/mole), JEFFAMINE HK-511 (i.e., polyetherdiamine with both oxyethylene and oxypropylene groups and having an average molecular weight of 220 g/mole), JEFFAMINE ED-2003 (i.e., polypropylene oxide capped polyethylene glycol having an average molecular weight of 2,000 g/mole), and JEFFAMINE EDR-148 (i.e., triethyleneglycol diamine).

Exemplary polyoxyalkylene triamines include, but are not limited to, those available, for example, from Huntsman (The Woodlands, Tex.) under the trade designations JEFFAMINE T-3000 (i.e., polyoxypropylene triamine having an average molecular weight of 3000 g/mole), JEFFAMINE T-5000 (i.e., polyoxypropylene triamine having an average molecular weight of 5000 g/mole), and combinations thereof.

The reactions can be conducted using a plurality of precursors of Formula II (II-a or II-b), a plurality of precursors of Formula VII (VII-a or VII-b), a plurality of amine compounds, or a combination thereof. A plurality of precursors having different average molecular weights can be combined under reaction conditions with a single amine compound or a mixture of amine compounds (e.g., one or more diamines and/or polyamines). For example, the precursor of Formula II (II-a or II-b) may include a mixture of materials with different values of n, different values of p, or different values of both n and p. The multiple amine compounds can include, for example, a first amine compound that is an organic diamine or polyamine and a second amine compound such as a polydiorganosiloxane diamine. Likewise, a single precursor can be combined under reaction conditions with multiple amine compounds.

The molar ratio of the precursor of Formula II (II-a or II-b) to the precursor of Formula VII (VII-a or VII-b) is often 1:1. For example, the molar ratio is often less than or equal to 1:0.80, less than or equal to 1:0.85, less than or equal to 1:0.90, less than or equal to 1:0.95, or less than or equal to 1:1. The molar ratio is often greater than or equal to 1:1.05, greater than or equal to 1:1.10, or greater than or equal to 1:1.15. For example, the molar ratio can be in the range of 1:0.80 to 1:1.20, in the range of 1:0.80 to 1:1.15, in the range of 1:0.80 to 1:1.10, in the range of 1:0.80 to 1:1.05, in the range of 1:0.90 to 1:1.10, or in the range of 1:0.95 to 1:1.05. Alternatively, the molar ratio of the precursor of Formula II to the precursor of Formula VII can be less than 1:1.20 or greater than 1:0.80. For example, it can be 1:0.50, 1:0.55, 1:0.60, 1:0.65, 1:0.70, or 1:0.75, or it can be 1:1.25, 1:1.30, or 1:1.35. For example, the molar ratio can be in the range of less than 1:1.20 down to and including 1:2.00. Alternatively, it can be in the range of greater than 1:0.80 up to and including 1:0.50. Varying the molar ratio can be used, for example, to alter the molecular weight of the polymer.

The molar ratio of the precursors of Formula II (II-a or II-b) and Formula VII (VII-a or VII-b) to the one or more amine compounds is often 1:1. For example, the molar ratio is often less than or equal to 1:0.80, less than or equal to 1:0.85, less than or equal to 1:0.90, less than or equal to 1:0.95, or less than or equal to 1:1. The molar ratio is often greater than or equal to 1:1.05, greater than or equal to 1:1.10, or greater than or equal to 1:1.15. For example, the molar ratio can be in the range of 1:0.80 to 1:1.20, in the range of 1:0.80 to 1:1.15, in the range of 1:0.80 to 1:1.10, in the range of 1:0.80 to 1:1.05, in the range of 1:0.90 to 1:1.10, or in the range of 1:0.95 to 1:1.05. Alternatively, the molar ratio of the precursor of Formula II and Formula VII to the one or more amine compounds can be less than 1:1.20 or greater than 1:0.80. For example, it can be 1:0.50, 1:0.55, 1:0.60, 1:0.65, 1:0.70, or 1:0.75, or it can be 1:1.25, 1:1.30, or 1:1.35. For example, the molar ratio can be in the range of less than 1:1.20 down to and including 1:2.00. Alternatively, it can be in the range of greater than 1:0.80 up to and including 1:0.50. Varying the molar ratio can be used, for example, to alter the overall molecular weight, which can effect the rheology of the resulting copolymers. Additionally, varying the molar ratio can be used to provide amide-containing end groups (e.g., oxalylamino-containing end groups) or amino end groups, depending upon which reactant is present in molar excess.

The condensation reaction of the precursor of Formula II (II-a or II-b), the precursor of Formula VII (VII-a or VII-b), and the one or more amine compounds is often conducted at room temperature or at elevated temperatures such as at temperatures up to 250° C. For example, the reaction often can be conducted at room temperature or at temperatures up to 100° C. In other examples, the reaction can be conducted at a temperature of at least 100° C., at least 120° C., or at least 150° C. For example, the reaction temperature is often in the range of 100° C. to 220° C., in the range of 120° C. to 220° C., or in the range of 150° C. to 200° C. The condensation reaction is often complete in less than 1 hour, in less than 2 hours, in less than 4 hours, in less than 8 hours, or in less than 12 hours.

The reactions can occur in the presence or absence of a solvent. Suitable solvents usually do not react with any of the reactants or products of the reactions. Additionally, suitable solvents are usually capable of maintaining all the reactants and all of the products in solution throughout the polymerization process. Exemplary solvents include, but are not limited to, toluene, tetrahydrofuran, dichloromethane, aliphatic hydrocarbons (e.g., alkanes such as hexane), or mixtures thereof.

Any solvent that is present can be stripped from the resulting polydiorganosiloxane polyamide at the completion of the reaction. Solvents that can be removed under the same conditions used to remove the alcohol by-product are often preferred. The stripping process is often conducted at a temperature of at least 100° C., at least 125° C., or at least 150° C. The stripping process is typically at a temperature less than 300° C., less than 250° C., or less than 225° C.

Conducting the reactions in the absence of a solvent can be desirable because only the volatile by-product, $R^2OH$, needs to be removed at the conclusion of the reaction. Additionally, a solvent that is not compatible with both reactants and the product can result in incomplete reaction and a low degree of polymerization.

Exemplary Method B-1

In one embodiment, the block copolymers having repeat units of Formula I-a and Formula VI-a can be prepared, for example, as follows. The method includes mixing together under reaction conditions: a) a precursor of Formula VIII-a:

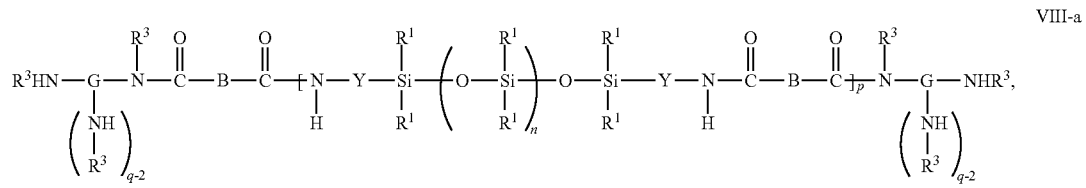

VIII-a and b) a precursor of Formula VII-a:

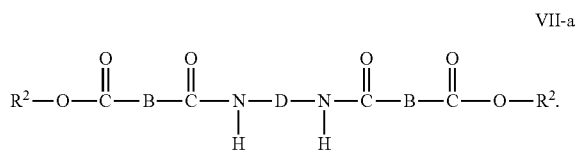

Exemplary Method B-2

In another embodiment, the block copolymers having repeat units of Formula I-b and Formula VI-b can be prepared, for example, as follows. The method includes mixing together under reaction conditions: a) a precursor of Formula VIII-b:

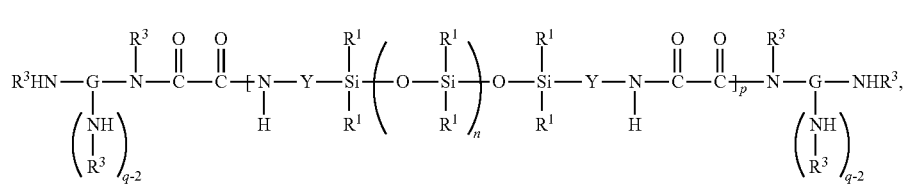

and b) a precursor of Formula VII-b:

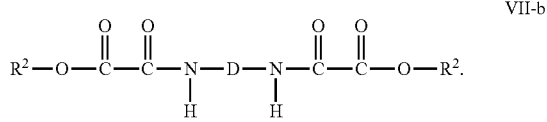

In Exemplary Method B (B-1 and B-2), a precursor of Formula VIII (VIII-a or VIII-b) and a precursor of Formula VII (VII-a and VII-b) are combined under reaction conditions. An additional amine need not be used in Exemplary Method B (B-1 and B-2). Precursors of Formula VII (VII-a and VII-b) are described above with respect to Exemplary Method A (A-1 and A-2).

The precursor of Formula VIII (VIII-a and VIII-b) have at least one polydiorganosiloxane segment, at least two amido groups (e.g., oxalylamino groups), and are amine terminated. The precursor of Formula VIII-a or VIII-b can be prepared, for example, by reacting a precursor of Formula II-a or II-b, respectively, with one or more amine compounds having on average the formula $G(NHR^3)_r$. Precursors of Formula II (II-a and II-b) and the one or more amine compounds having on average the formula $G(NHR^3)_r$ are described above with respect to Exemplary Method A (A-1 and A-2).

The reactions can be conducted using a plurality of precursors of Formula VIII (VIII-a or VIII-b) and/or a plurality of precursors of Formula VII (VII-a or VII-b). A plurality of precursors having different average molecular weights can be combined under reaction conditions. For example, the precursor of Formula VIII (VIII-a or VIII-b) may include a mixture of materials with different values of n, different values of p, or different values of both n and p.

The molar ratio of the precursor of Formula VIII (VIII-a or VIII-b) to the precursor of Formula VII (VII-a or VII-b) is often 1:1. For example, the molar ratio is often less than or equal to 1:0.80, less than or equal to 1:0.85, less than or equal to 1:0.90, less than or equal to 1:0.95, or less than or equal to 1:1. The molar ratio is often greater than or equal to 1:1.05, greater than or equal to 1:1.10, or greater than or equal to 1:1.15. For example, the molar ratio can be in the range of 1:0.80 to 1:1.20, in the range of 1:0.80 to 1:1.15, in the range of 1:0.80 to 1:1.10, in the range of 1:0.80 to 1:1.05, in the range of 1:0.90 to 1:1.10, or in the range of 1:0.95 to 1:1.05. Alternatively, the molar ratio of the precursor of Formula VIII to the precursor of Formula VII can be less than 1:1.20 or greater than 1:0.80. For example, it can be 1:0.50, 1:0.55, 1:0.60, 1:0.65, 1:0.70, or 1:0.75, or it can be 1:1.25, 1:1.30, or 1:1.35. For example, the molar ratio can be in the range of less than 1:1.20 down to and including 1:2.00. Alternatively, it can be in the range of greater than 1:0.80 up to and including 1:0.50. Varying the molar ratio can be used, for example, to alter the molecular weight, melt rheology, surface properties, and/or refractive index of the resulting polymer. Additionally, varying the molar ratio can be used to provide amide-containing end groups (e.g., oxalylamino-containing end groups) or amino end groups, depending upon which reactant is present in molar excess.

The condensation reaction of the precursor of Formula VIII (VIII-a or VIII-b) and the precursor of Formula VII (VII-a or VII-b) is often conducted at room temperature or at elevated temperatures such as at temperatures up to 250° C. For example, the reaction often can be conducted at room temperature or at temperatures up to 100° C. In other examples, the reaction can be conducted at a temperature of at least 100° C., at least 120° C., or at least 150° C. For example, the reaction temperature is often in the range of 100° C. to 220° C., in the range of 120° C. to 220° C., or in the range of 150° C. to 200° C. The condensation reaction is often complete in less than 1 hour, in less than 2 hours, in less than 4 hours, in less than 8 hours, or in less than 12 hours.

The reactions can occur in the presence or absence of a solvent. Suitable solvents usually do not react with any of the reactants or products of the reactions. Additionally, suitable solvents are usually capable of maintaining all the reactants and all of the products in solution throughout the polymerization process. Exemplary solvents include, but are not limited to, toluene, tetrahydrofuran, dichloromethane, aliphatic hydrocarbons (e.g., alkanes such as hexane), or mixtures thereof.

Any solvent that is present can be stripped from the resulting polydiorganosiloxane polyamide at the completion of the reaction. Solvents that can be removed under the same conditions used to remove the alcohol by-product are often preferred. The stripping process is often conducted at a temperature of at least 100° C., at least 125° C., or at least 150° C. The stripping process is typically at a temperature less than 300° C., less than 250° C., or less than 225° C.

Conducting the reactions in the absence of a solvent can be desirable because only the volatile by-product, $R^2OH$, needs to be removed at the conclusion of the reaction. Additionally, a solvent that is not compatible with both reactants and the product can result in incomplete reaction and a low degree of polymerization.

Any suitable reactor or process can be used to prepare the copolymeric material according to all of the exemplary methods disclosed herein. The reaction can be conducted using a batch process, semi-batch process, or a continuous process. Exemplary batch processes can be conducted in a reaction vessel equipped with a mechanical stirrer such as a Brabender mixer, provided the product of the reaction is in a molten state has a sufficiently low viscosity to be drained from the reactor. Exemplary semi-batch process can be conducted in a continuously stirred tube, tank, or fluidized bed. Exemplary continuous processes can be conducted in a single screw or twin screw extruder such as a wiped surface counter-rotating or co-rotating twin screw extruder.

In many processes, the components are metered and then mixed together to form a reaction mixture. The components can be metered volumetrically or gravimetrically using, for example, a gear, piston or progressing cavity pump. The components can be mixed using any known static or dynamic method such as, for example, static mixers, or compounding mixers such as single or multiple screw extruders. The reaction mixture can then be formed, poured, pumped, coated, injection molded, sprayed, sputtered, atomized, stranded or sheeted, and partially or completely polymerized. The partially or completely polymerized material can then optionally be converted to a particle, droplet, pellet, sphere, strand, ribbon, rod, tube, film, sheet, coextruded film, web, nonwoven, microreplicated structure, or other continuous or discrete shape, prior to the transformation to solid polymer. Any of these steps can be conducted in the presence or absence of applied heat. In one exemplary process, the components can be metered using a gear pump, mixed using a static mixer, and injected into a mold prior to solidification of the polymerizing material.

The polydiorganosiloxane-containing precursor of Formula II-b can be prepared by any known method. In some embodiments, this precursor is prepared according to Reaction Scheme A.

in U.S. patent application Ser. No. 11/317,616, filed 23 Dec. 2005.

The polydiorganosiloxane diamine of Formula III in Reaction Scheme A can be prepared by any known method and can have any suitable molecular weight, such as an average molecular weight in the range of 700 to 150,000 g/mole. Suitable polydiorganosiloxane diamines and methods of making the polydiorganosiloxane diamines are described, for example, in U.S. Pat. No. 3,890,269 (Martin), U.S. Pat. No. 4,661,577 (Jo Lane et al.), U.S. Pat. No. 5,026,890 (Webb et al.), U.S. Pat. No. 5,276,122 (Aoki et al.), U.S. Pat. No. 5,214,119 (Leir et al.), U.S. Pat. No. 5,461,134 (Leir et al.), U.S. Pat. No. 5,512,650 (Leir et al.), and U.S. Pat. No. 6,355,759 (Sherman et al.). Some polydiorganosiloxane diamines are commercially available, for example, from Shin Etsu Silicones of America, Inc., Torrance, Calif. and from Gelest Inc., Morrisville, Pa.

A polydiorganosiloxane diamine having a molecular weight greater than 2,000 g/mole or greater than 5,000 g/mole can be prepared using the methods described in U.S. Pat. No. 5,214,119 (Leir et al.), U.S. Pat. No. 5,461,134 (Leir et al.), and U.S. Pat. No. 5,512,650 (Leir et al.). One of the described methods involves combining under reaction conditions and under an inert atmosphere (a) an amine functional end blocker of the following formula

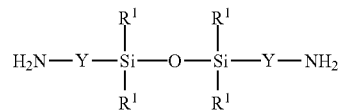

where Y and $R^1$ are the same as defined for Formula I (I-a or I-b); (b) sufficient cyclic siloxane to react with the amine functional end blocker to form a polydiorganosiloxane diamine having a molecular weight less than 2,000 g/mole; and (c) an anhydrous aminoalkyl silanolate catalyst of the following formula Reaction Scheme A

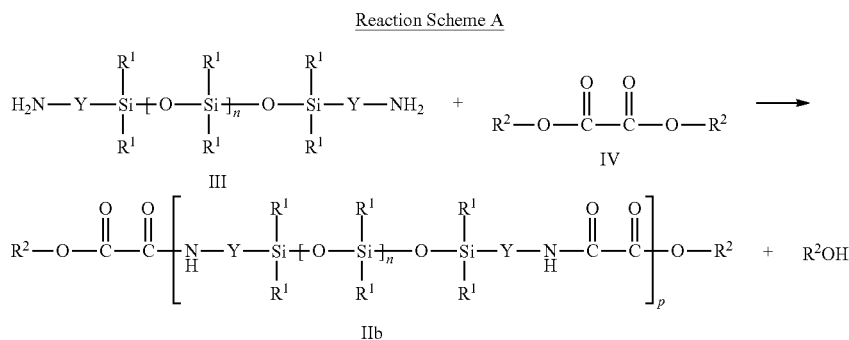

A polydiorganosiloxane diamine of Formula III (p moles) is reacted with a molar excess of an oxalate of Formula IV (greater than p+1 moles) under an inert atmosphere to produce the polydiorganosiloxane-containing precursor of Formula II and $R^2$—OH by-product. In this reaction, $R^1$, Y, n, and p are the same as previously described for Formula I (I-a or I-b). Each $R^2$ in Formula IV is independently an alkyl, haloalkyl, aryl, or aryl substituted with an alkyl, alkoxy, halo, or alkoxycarbonyl. The preparation of the precursor of Formula II according to Reaction Scheme A is further described

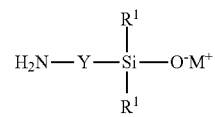

where Y and $R^1$ are the same as defined in Formula I (I-a or I-b) and $M^+$ is a sodium ion, potassium ion, cesium ion, rubidium ion, or tetramethylammonium ion. The reaction is continued until substantially all of the amine functional end blocker is consumed and then additional cyclic siloxane is added to increase the molecular weight. The additional cyclic siloxane is often added slowly (e.g., drop wise). The reaction temperature is often conducted in the range of 80° C. to 90° C. with a reaction time of 5 to 7 hours. The resulting polydiorganosiloxane diamine can be of high purity (e.g., less than 2 weight percent, less than 1.5 weight percent, less than 1 weight percent, less than 0.5 weight percent, less than 0.1 weight percent, less than 0.05 weight percent, or less than 0.01 weight percent silanol impurities). Altering the ratio of the amine end functional blocker to the cyclic siloxane can be used to vary the molecular weight of the resulting polydiorganosiloxane diamine of Formula III.

Another method of preparing the polydiorganosiloxane diamine of Formula III includes combining under reaction conditions and under an inert environment (a) an amine functional end blocker of the following formula

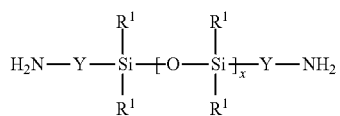

where $R^1$ and Y are the same as described for Formula I (I-a or I-b) and where the subscript x is equal to an integer of 1 to 150; (b) sufficient cyclic siloxane to obtain a polydiorganosiloxane diamine having an average molecular weight greater than the average molecular weight of the amine functional end blocker; and (c) a catalyst selected from cesium hydroxide, cesium silanolate, rubidium silanolate, cesium polysiloxanolate, rubidium polysiloxanolate, and mixtures thereof. The reaction is continued until substantially all of the amine functional end blocker is consumed. This method is further described in U.S. Pat. No. 6,355,759 B1 (Sherman et al.). This procedure can be used to prepare any molecular weight of the polydiorganosiloxane diamine.

Yet another method of preparing the polydiorganosiloxane diamine of Formula III is described in U.S. Pat. No. 6,531,620 B2 (Brader et al.). In this method, a cyclic silazane is reacted with a siloxane material having hydroxy end groups as shown in the following reaction.

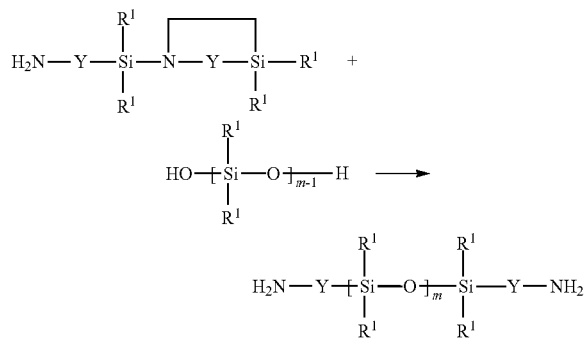

The groups $R^1$ and Y are the same as described for Formula I (I-a or I-b). The subscript m is an integer greater than 1.

Examples of polydiorganosiloxane diamines include, but are not limited to, polydimethylsiloxane diamine, polydiphenylsiloxane diamine, polytrifluoropropylmethylsiloxane diamine, polyphenylmethylsiloxane diamine, polydiethylsiloxane diamine, polydivinylsiloxane diamine, polyvinylmethylsiloxane diamine, poly(5-hexenyl)methylsiloxane diamine, and mixtures thereof.

In Reaction Scheme A, an oxalate of Formula IV is reacted with the polydiorganosiloxane diamine of Formula III under an inert atmosphere. The two $R^2$ groups in the oxalate of Formula IV can be the same or different. In some methods, the two $R^2$ groups are different and have different reactivity with the polydiorganosiloxane diamine of Formula III in Reaction Scheme A.

Group $R^2$ can be an alkyl, haloalkyl, aryl, or aryl substituted with an alkyl, alkoxy, halo, or alkoxycarbonyl. Suitable alkyl and haloalkyl groups for $R^2$ often have 1 to 10, 1 to 6, or 1 to 4 carbon atoms. Although tertiary alkyl (e.g., tert-butyl) and haloalkyl groups can be used, there is often a primary or secondary carbon atom attached directly (i.e., bonded) to the adjacent oxy group. Exemplary alkyl groups include methyl, ethyl, n-propyl, iso-propyl, n-butyl, and iso-butyl. Exemplary haloalkyl groups include chloroalkyl groups and fluoroalkyl groups in which some, but not all, of the hydrogen atoms on the corresponding alkyl group are replaced with halo atoms. For example, the chloroalkyl or a fluoroalkyl groups can be chloromethyl, 2-chloroethyl, 2,2,2-trichloroethyl, 3-chloropropyl, 4-chlorobutyl, fluoromethyl, 2-fluoroethyl, 2,2,2-trifluoroethyl, 3-fluoropropyl, 4-fluorobutyl, and the like. Suitable aryl groups for $R^2$ include those having 6 to 12 carbon atoms such as, for example, phenyl. An aryl group can be unsubstituted or substituted with an alkyl (e.g., an alkyl having 1 to 4 carbon atoms such as methyl, ethyl, or n-propyl), an alkoxy (e.g., an alkoxy having 1 to 4 carbon atoms such as methoxy, ethoxy, or propoxy), halo (e.g., chloro, bromo, or fluoro), or alkoxycarbonyl (e.g., an alkoxycarbonyl having 2 to 5 carbon atoms such as methoxycarbonyl, ethoxycarbonyl, or propoxycarbonyl).

The oxalates of Formula IV in Reaction Scheme A can be prepared, for example, by reaction of an alcohol of formula $R^2$—OH with oxalyl dichloride. Commercially available oxalates of Formula IV (e.g., from Sigma-Aldrich, Milwaukee, Wis. and from VWR International, Bristol, Conn.) include, but are not limited to, dimethyl oxalate, diethyl oxalate, di-n-butyl oxalate, di-tert-butyl oxalate, bis(phenyl) oxalate, bis(pentafluorophenyl)oxalate, 1-(2,6-difluorophenyl)-2-(2,3,4,5,6-pentachlorophenyl)oxalate, and bis(2,4,6-trichlorophenyl)oxalate.

A molar excess of the oxalate is used in Reaction Scheme A. That is, the molar ratio of oxalate to polydiorganosiloxane diamine is greater than the stoichiometric molar ratio, which is (p+1):p. The molar ratio is often greater than 2:1, greater than 3:1, greater than 4:1, or greater than 6:1. The condensation reaction typically occurs under an inert atmosphere and at room temperature upon mixing of the components.

The condensation reaction used to produce the precursor of Formula II (i.e., Reaction Scheme A) can occur in the presence or absence of a solvent. In some methods, no solvent or only a small amount of solvent is included in the reaction mixture. In other methods, a solvent may be included such as, for example, toluene, tetrahydrofuran, dichloromethane, or aliphatic hydrocarbons (e.g., alkanes such as hexane).

Removal of excess oxalate from the precursor of Formula II prior to reaction with the diamine tends to favor formation of an optically clear polydiorganosiloxane polyamide. The excess oxalate can typically be removed from the precursor using a stripping process. For example, the reacted mixture (i.e., the product or products of the condensation reaction according to Reaction Scheme A) can be heated to a temperature up to 150° C., up to 175° C., up to 200° C., up to 225° C., or up to 250° C. to volatilize the excess oxalate. A vacuum can be pulled to lower the temperature that is needed for removal of the excess oxalate. The precursor compounds of Formula II tend to undergo minimal or no apparent degradation at temperatures in the range of 200° C. to 250° C. or higher. Any other known methods of removing the excess oxalate can be used.

The by-product of the condensation reaction shown in Reaction Scheme A is an alcohol (i.e., $R^2$—OH is an alcohol). Group $R^2$ is often limited to an alkyl having 1 to 4 carbon atoms, a haloalkyl having 1 to 4 carbon atoms, or an aryl such as phenyl that form an alcohol that can be readily removed (e.g., vaporized) by heating at temperatures no greater than 250° C. Such an alcohol can be removed when the reacted mixture is heated to a temperature sufficient to remove the excess oxalate of Formula IV.

Compositions and Constructions

The polydiorganosiloxane polyamide copolymers having amide end-capped (e.g., oxalated) organic soft segments can be blended with one or more other polymers (e.g., organic polymer components) such as a hot melt processable thermoplastic polymer (which may be elastomeric or nonelastomeric), a hot melt processable elastomeric thermoset polymer, a silicone polymer, and mixtures thereof.

The organic polymer may be solvent or melt mixed with the polydiorganosiloxane polyamide segmented copolymer. The organic polymer may be a polydiorganosiloxane polyamide-containing component or a polymer that does not contain polydiorganosiloxane segments.

Examples of suitable polydiorganosiloxane polyamide-containing components include linear and/or branched polydiorganosiloxane polyamide copolymers. An exemplary linear copolymeric material contains at least two repeat units of Formula V-a:

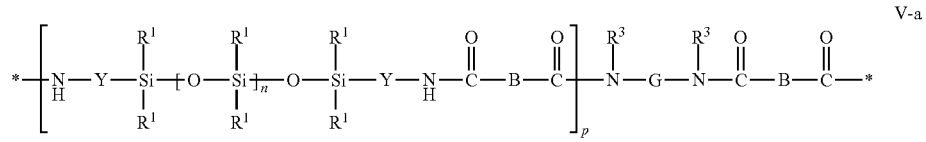

In this formula, each $R^1$ is independently an alkyl, haloalkyl, aralkyl, alkenyl, aryl, or aryl substituted with an alkyl, alkoxy, or halo. Each Y is independently an alkylene, aralkylene, or a combination thereof. Subscript n is independently an integer of 0 to 1500 and subscript p is an integer of 1 to 10. Group G is a divalent group that is the residue unit that is equal to a diamine of formula $R^3$HN-G-NHR$^3$ minus the two —NHR$^3$ groups (i.e., amino groups). Group $R^3$ is hydrogen or alkyl or $R^3$ taken together with G and with the nitrogen to which they are both attached forms a heterocyclic group. Each B is independently a covalent bond, an alkylene of 4-20 carbons, an aralkylene, an arylene, or a combination thereof. Each asterisk indicates the position of attachment of the repeating unit to another group such as another repeat unit.

A preferred copolymeric material contains at least two repeat units of Formula V-b:

In this formula, each $R^1$ is independently an alkyl, haloalkyl, aralkyl, alkenyl, aryl, or aryl substituted with an alkyl, alkoxy, or halo. Each Y is independently an alkylene, aralkylene, or a combination thereof. Subscript n is independently an integer of 0 to 1500 and subscript p is an integer of 1 to 10. Group G is a divalent group that is the residue unit that is equal to a diamine of formula $R^3$HN-G-NHR$^3$ minus the two —NHR$^3$ groups (i.e., amino groups). Group $R^3$ is hydrogen or alkyl or $R^3$ taken together with G and with the nitrogen to which they are both attached forms a heterocyclic group. Each asterisk indicates the position of attachment of the repeating unit to another group such as another repeat unit.

Thermoplastic materials useful in the present invention that are generally considered nonelastomeric include, for example, polyolefins such as isotactic polypropylene, low density polyethylene, linear low density polyethylene, very low density polyethylene, medium density polyethylene, high density polyethylene, polybutylene, nonelastomeric polyolefin copolymers or terpolymers, such as ethylene/propylene copolymer and blends thereof; ethylene-vinyl acetate copolymers such as that available under the trade designation ELVAX 260, available from DuPont Chemical Co.; ethylene acrylic acid copolymers; ethylene methacrylic acid copolymers such as that available under the trade designation SURLYN 1702, available from DuPont Chemical Co.; polymethylmethacrylate; polystyrene; ethylene vinyl alcohol; polyester; amorphous polyester; polyamides; fluorinated thermoplastics, such a polyvinylidene fluoride, polytetrafluoroethylene, fluorinated ethylene/propylene copolymers and fluorinated ethylene/propylene copolymers; halogenated thermoplastics, such as a chlorinated polyethylene. Any single thermoplastic material can be mixed with at least one branched polydiorganosiloxane polyamide-containing component. Alternatively, a mixture of thermoplastic materials may be used.

Thermoplastic materials that have elastomeric properties are typically called thermoplastic elastomeric materials. Thermoplastic elastomeric materials are generally defined as materials that act as though they were covalently cross-linked, exhibiting high resilience and low creep, yet flow when heated above their softening point. Thermoplastic elastomeric materials useful in the present invention include, for example, linear, radial, star and tapered styrene-isoprene block copolymers such as that available under the trade designation KRATON D1107P from Shell Chemical Co. of Houston, Tex. and that available under the trade designation EUROPRENE SOL TE 9110 from EniChem Elastomers Americas, Inc. of Houston, Tex.; linear styrene-(ethylene-

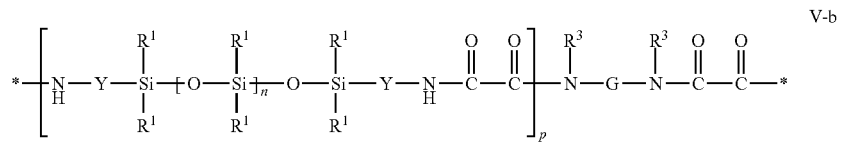

butylene) block copolymers such as that available under the trade designation KRATON G1657 from Shell Chemical Co.; linear styrene-(ethylene-propylene) block copolymers such as that available under the trade designation KRATON G1657X from Shell Chemical Co.; linear, radial, and star styrene-butadiene block copolymers such as that available under the trade designation KRATON D1118X from Shell Chemical Co. and that available under the trade designation EUROPRENE SOL TE 6205 from EniChem Elastomers Americas, Inc.; polyetheresters such as that available under the trade designation HYTREL G3548 from DuPont, elastomeric ethylene-propylene copolymers; thermoplastic elastomeric polyurethanes such as that available under the trade designation MORTHANE URETHENE PE44-203 from Morton International, Inc., Chicago, Ill.; self-tacky or tackified polyacrylates including $C_3$ to $C_{12}$ alkylesters that may contain other comonomers, such as for example, isooctyl acrylate and from 0 to 20 weight percent acrylic acid; polyvinylethers; poly-α-olefin-based thermoplastic elastomeric materials such as those represented by the formula —$(CH_2CHR)_x$ where R is an alkyl group containing 2 to 10 carbon atoms and poly-α-olefins based on metallocene catalysis such as that available under the trade designation ENGAGE EG8200, an ethylene/poly-α-olefin copolymer, available from Dow Plastics Co. of Midland, Mich.; as well as polydiorganosiloxane polyurea-urethanes, available from Wacker Chemie AG, Germany under the trade designation GENIOMER.

Thermoset elastomers (i.e., elastomeric thermosets) are materials that change irreversibly under the influence of heat from a fusible and soluble material into one that is infusible and insoluble through the formation of a covalently cross-linked, thermally stable network. Thermoset elastomers useful in the present invention include, for example, natural rubbers such as CV-60, a controlled viscosity grade available from Goodyear Chemical, Akron, Ohio, and SMR-5, a ribbed smoked sheet rubber; butyl rubbers, such as Exxon Butyl 268 available from Exxon Chemical Co.; synthetic polyisoprenes such as that available under the trade designation CARIFLEX IR309 from Royal Dutch Shell of Netherlands and that available under the trade designation NATSYN 2210 from Goodyear Tire and Rubber Co.; styrene-butadiene random copolymer rubbers such as that available under the trade designation AMERIPOL 1011A from BF Goodrich of Akron, Ohio; polybutadienes; polyisobutylenes such as that available under the trade designation VISTANEX MM L-80 from Exxon Chemical Co.; polyurethanes such as, for example, polyoctadecyl carbamate disclosed in U.S. Pat. No. 2,532,011 (Dahlquist et al.); amorphous poly-α-olefins such as $C_4$-$C_{10}$ linear or branched poly-α-olefins; polydiorganosiloxane polyurea-containing components, such as those disclosed in U.S. Pat. No. 5,214,119 (Leir et al.).

Suitable silicone polymers are typically fluids and may be curable (through incorporation of suitable functional groups such as hydroxyl groups or ethylenically unsaturated groups, e.g., acrylate groups) or substantially noncurable. Examples of suitable silicone fluids are described in, for example, International Publication No. WO 97/40103, U.S. Pat. No. 6,441,118, U.S. Pat. No. 5,091,483, and U.S. Pat. Pub. No. 2005/0136266. Particularly preferred silicone polymers are moisture-curable silicone fluids, e.g., hydroxyl-terminated polydiorganosiloxanes or nonreactive silicone fluids such as that available under the trade designation 47V1000 RHODORSIL from Rhodia Silicones. Any of the hydroxyl-terminated polydiorganosiloxanes typically used in known silicone sealing and adhesive compositions may be used in the compositions of the present invention. Examples of suitable commercially available silicone fluids include those available under the trade designation MASIL from Lubruzol Corp. (Ohio) and Wacker Chemie AG (Germany).

Compositions and constructions as disclosed herein can also include functional components. Functional components such as antistatic additives, ultraviolet light absorbers (UVAs), hindered amine light stabilizers (HALS), dyes, colorants, pigments, antioxidants, slip agents, low adhesion materials, conductive materials, abrasion resistant materials, optical elements, dimensional stabilizers, adhesives, tackifiers, flame retardants, phosphorescent materials, fluorescent materials, nanoparticles, anti-graffiti agents, dew-resistant agents, load bearing agents, silicate resins, fumed silica, glass beads, glass bubbles, glass fibers, mineral fibers, clay particles, organic fibers, e.g., nylon, KEVLAR, metal particles, and the like which can be added in amounts up to 100 parts per 100 parts of the sum of the branched polydiorganosiloxane polyamide segmented polymeric component, provided that if and when incorporated, such additives are not detrimental to the function and functionality of the final polymer product. Other additives such as light diffusing materials, light absorptive materials and optical brighteners, flame retardants, stabilizers, antioxidants, compatibilizers, antimicrobial agents such as zinc oxide, electrical conductors, thermal conductors such as aluminum oxide, boron nitride, aluminum nitride, and nickel particles, including organic and/or inorganic particles, or any number or combination thereof can be blended into these systems. The functional components listed above may also be incorporated into polydiorganosiloxane polyamide block copolymer provided such incorporation does not adversely affect any of the resulting product to an undesirable extent.

Fillers, tackifiers, plasticizers, and other property modifiers may be incorporated in the branched, polydiorganosiloxane polyamide segmented organic polymer. Tackifying materials or plasticizers useful with the polymeric materials are preferably miscible at the molecular level, e.g., soluble in, any or all of the polymeric segments of the elastomeric material or the thermoplastic elastomeric material. These tackifying materials or plasticizers are generally immiscible with the polydiorganosiloxane polyamide-containing component. When the tackifying material is present it generally comprises 5 to 300 parts by weight, more typically up to 200 parts by weight, based on 100 parts by weight of the polymeric material. Examples of tackifiers suitable for the invention include but are not limited to liquid rubbers, hydrocarbon resins, rosin, natural resins such as dimerized or hydrogenated balsams and esterified abietic acids, polyterpenes, terpene phenolics, phenol-formaldehyde resins, and rosin esters. Examples of plasticizers include but are not limited to polybutene, paraffinic oils, petrolatum, and certain phthalates with long aliphatic side chains such as ditridecyl phthalate.

Either pressure sensitive adhesives or heat activated adhesives can be formulated by combining the polydiorganosiloxane polyoxamides with a tackifier such as a silicate tackifying resin. As used herein, the term "pressure sensitive adhesive" refers to an adhesive that possesses the following properties: (1) aggressive and permanent tack; (2) adherence to a substrate with no more than finger pressure; (3) sufficient ability to hold onto an adherend; and (4) sufficient cohesive strength to be removed cleanly from the adherend. As used herein, the term "heat activated adhesive" refers to an adhesive composition that is essentially non-tacky at room temperature but that becomes tacky above room temperature above an activation temperature such as above 30° C. Heat activated adhesives typically have the properties of a pressure sensitive adhesive above the activation temperature.

Tackifying resins such as silicate tackifying resins are added to the polydiorganosiloxane polyoxamide copolymer to provide or enhance the adhesive properties of the copolymer. The silicate tackifying resin can influence the physical properties of the resulting adhesive composition. For example, as silicate tackifying resin content is increased, the glassy to rubbery transition of the adhesive composition occurs at increasingly higher temperatures. In some exemplary adhesive compositions, a plurality of silicate tackifying resins can be used to achieve desired performance.

Suitable silicate tackifying resins include those resins composed of the following structural units M (i.e., monovalent $R'_3SiO_{1/2}$ units), D (i.e., divalent $R'_2SiO_{2/2}$ units), T (i.e., trivalent $R'SiO_{3/2}$ units), and Q (i.e., quaternary $SiO_{4/2}$ units), and combinations thereof. Typical exemplary silicate resins include MQ silicate tackifying resins, MQD silicate tackifying resins, and MQT silicate tackifying resins. These silicate tackifying resins usually have a number average molecular weight in the range of 100 to 50,000 or in the range of 500 to 15,000 and generally have methyl R' groups.

MQ silicate tackifying resins are copolymeric resins having $R'_3SiO_{1/2}$ units ("M" units) and $SiO_{4/2}$ units ("Q" units), where the M units are bonded to the Q units, each of which is bonded to at least one other Q unit. Some of the $SiO_{4/2}$ units ("Q" units) are bonded to hydroxyl radicals resulting in $HOSiO_{3/2}$ units ("$T^{OH}$" units), thereby accounting for the silicon-bonded hydroxyl content of the silicate tackifying resin, and some are bonded only to other $SiO_{4/2}$ units.

Such resins are described in, for example, *Encyclopedia of Polymer Science and Engineering*, vol. 15, John Wiley & Sons, New York, (1989), pp. 265-270, and U.S. Pat. No. 2,676,182 (Daudt et al.), U.S. Pat. No. 3,627,851 (Brady), U.S. Pat. No. 3,772,247 (Flannigan), and U.S. Pat. No. 5,248,739 (Schmidt et al.). Other examples are disclosed in U.S. Pat. No. 5,082,706 (Tangney). The above-described resins are generally prepared in solvent. Dried or solventless, M silicone tackifying resins can be prepared, as described in U.S. Pat. No. 5,319,040 (Wengrovius et al.), U.S. Pat. No. 5,302,685 (Tsumura et al.), and U.S. Pat. No. 4,935,484 (Wolfgruber et al.).

Certain MQ silicate tackifying resins can be prepared by the silica hydrosol capping process described in U.S. Pat. No. 2,676,182 (Daudt et al.) as modified according to U.S. Pat. No. 3,627,851 (Brady), and U.S. Pat. No. 3,772,247 (Flannigan). These modified processes often include limiting the concentration of the sodium silicate solution, and/or the silicon-to-sodium ratio in the sodium silicate, and/or the time before capping the neutralized sodium silicate solution to generally lower values than those disclosed by Daudt et al. The neutralized silica hydrosol is often stabilized with an alcohol, such as 2-propanol, and capped with $R_3SiO_{1/2}$ siloxane units as soon as possible after being neutralized. The level of silicon bonded hydroxyl groups (i.e., silanol) on the MQ resin may be reduced to no greater than 1.5 weight percent, no greater than 1.2 weight percent, no greater than 1.0 weight percent, or no greater than 0.8 weight percent based on the weight of the silicate tackifying resin. This may be accomplished, for example, by reacting hexamethyldisilazane with the silicate tackifying resin. Such a reaction may be catalyzed, for example, with trifluoroacetic acid. Alternatively, trimethylchlorosilane or trimethylsilylacetamide may be reacted with the silicate tackifying resin, a catalyst not being necessary in this case.

MQD silicone tackifying resins are terpolymers having $R'_3SiO_{1/2}$ units ("M" units), $SiO_{4/2}$ units ("Q" units), and $R'_2SiO_{2/2}$ units ("D" units) such as are taught in U.S. Pat. No. 2,736,721 (Dexter). In MQD silicone tackifying resins, some of the methyl R' groups of the $R'_2SiO_{2/2}$ units ("D" units) can be replaced with vinyl ($CH_2=CH-$) groups ("$D^{Vi}$" units).

MQT silicate tackifying resins are terpolymers having $R'_3SiO_{1/2}$ units, $SiO_{4/2}$ units and $R'SiO_{3/2}$ units ("T" units) such as are taught in U.S. Pat. No. 5,110,890 (Butler) and Japanese Kokai HE 2-36234.

Suitable silicate tackifying resins are commercially available from sources such as Dow Corning, Midland, Mich., General Electric Silicones Waterford, N.Y. and Rhodia Silicones, Rock Hill, S.C. Examples of particularly useful MQ silicate tackifying resins include those available under the trade designations SR-545 and SR-1000, both of which are commercially available from GE Silicones, Waterford, N.Y. Such resins are generally supplied in organic solvent and may be employed in the formulations of the adhesives of the present invention as received. Blends of two or more silicate resins can be included in the adhesive compositions.

The adhesive compositions typically contain 20 to 80 weight percent polydiorganosiloxane polyoxamide and 20 to 80 weight percent silicate tackifying resin based on the combined weight of polydiorganosiloxane polyoxamide and silicate tackifying resin. For example, the adhesive compositions can contain 30 to 70 weight percent polydiorganosiloxane polyoxamide and 30 to 70 weight percent silicate tackifying resin, 35 to 65 weight percent polydiorganosiloxane polyoxamide and 35 to 65 weight percent silicate tackifying resin, 40 to 60 weight percent polydiorganosiloxane polyoxamide and 40 to 60 weight percent silicate tackifying resin, or 45 to 55 weight percent polydiorganosiloxane polyoxamide and 45 to 55 weight percent silicate tackifying resin.

The adhesive composition can be solvent-free or can contain a solvent. Suitable solvents include, but are not limited to, toluene, tetrahydrofuran, dichloromethane, aliphatic hydrocarbons (e.g., alkanes such as hexane), or mixtures thereof.

Polydiorganosiloxane polyamides with a small amount of branching can be soluble in many common organic solvents such as, for example, toluene, tetrahydrofuran, dichloromethane, aliphatic hydrocarbons (e.g., alkanes such as hexane), or mixtures thereof. Polydiorganosiloxane polyamides with higher amounts of branching can be swellable in many common organic solvents such as, for example, toluene, tetrahydrofuran, dichloromethane, aliphatic hydrocarbons (e.g., alkanes such as hexane), or mixtures thereof.

The polydiorganosiloxane polyamides can be cast from solvents as film, molded or embossed in various shapes, or extruded into films. The high temperature stability of the copolymeric material makes them well suited for extrusion methods of film formation. The films can be optically clear. A multilayer film containing the polydiorganosiloxane polyamide block copolymers is further described in U.S. patent application Ser. No. 11/614,169, filed 21 Dec. 2006.

Processes of Making Compositions and Constructions

The compositions and constructions disclosed herein can be made by solvent-based processes known to the art, by a solventless process, or by a combination of the two.

For embodiments in which the composition or construction includes, for example, an organic polymer, one skilled in the art can expect the optimum material for a particular application to be a function of the architecture and ratios of the polydiorganosiloxane polyamide-containing component, the architecture and ratios of organic polymer, optional initiator architecture, and whether any fillers, additives, or property modifiers are added.

For embodiments in which the composition or construction includes an organic polymer, the organic polymer is generally added as a molten stream to the polydiorganosiloxane polyamide-containing component or to one of the reactants of the polydiorganosiloxane polyamide-containing component. Sometimes the polymeric material needs to be melted in a separate vessel before the polydiorganosiloxane polyamide-containing component is added (1) as pellets, (2) as reactants or (3) as a separate molten stream from a second vessel. Examples when a separate vessel is preferred include, for example, when (1) additives are preferred to concentrate in the organic polymer, (2) organic polymers need high processing temperatures and (3) organic polymers include elastomeric thermoset materials.

The order of adding the various components is important in forming the mixture. For embodiments in which the composition or construction includes an organic polymer, any order of addition can be used if the organic polymer is substantially unreactive with the reactants for making the polydiorganosiloxane polyamide (e.g., diamines) as discussed earlier. The polydiorganosiloxane polyamide-containing component can be added to the organic polymer, and vice versa, or the polydiorganosiloxane polyamide-containing component can be made in the presence of the organic polymer. However, the organic polymer must be added after the polydiorganosiloxane polyamide-containing component is formed if the organic polymer is reactive with the reactants for making such component. Also, the organic polymer is preferably sufficiently heated to a processable state in a separate vessel and added to a molten stream of the polydiorganosiloxane polyamide-containing component if the temperature needed to process the organic polymer would degrade the polydiorganosiloxane polyamide-containing component.

Other additives such as plasticizing materials, tackifying materials, pigments, fillers, initiators, and the like can generally be added at any point in the process since they are usually not reactive with the reactants but are typically added after a substantial amount of the polydiorganosiloxane polyamide-containing component is formed.

For embodiments in which the composition or construction includes an organic polymer, organic polymers that are non-thermoplastic elastomeric materials generally need special conditions to be melt processed when mixed with polydiorganosiloxane polyamide-containing components. Two methods of making non-thermoplastic elastomeric materials melt processable are (1) reducing their apparent melt viscosity by swelling them with tackifying or plasticizing material or (2) masticating the materials as described in U.S. Pat. No. 5,539,033.

Four process considerations can affect the final properties of the mixtures made by the solventless process. First, the properties of polydiorganosiloxane polyamide-containing component could be affected by whether the polydiorganosiloxane polyamide-containing component is made in a solvent or an essentially solventless process. Secondly, the polydiorganosiloxane polyamide-containing component can degrade if exposed to too much heat and shear. Thirdly, the stability of the mixture is affected by how the polydiorganosiloxane polyamide-containing component is mixed with the organic polymer. Fourthly, the morphology of the article made with the mixture is determined by the interaction of the processing parameters and characteristics of the components in the mixture.

In a first consideration, the polydiorganosiloxane polyamide-containing component can be made previously by either a solvent or solventless process or can be made in the presence of the organic polymer. Methods of making the polydiorganosiloxane polyamide-containing component in solvent were disclosed above. Methods of making the polydiorganosiloxane polyamide-containing component in substantially solventless conditions can result in polydiorganosiloxane polyamide-containing component high in molecular weight In a second consideration, the polydiorganosiloxane polyamide-containing component can degrade if it is heated too much under shear conditions, particularly in the presence of oxygen. The polydiorganosiloxane polyamide-containing component is exposed to the least amount of heat and shear when made in the presence of the organic polymer, and in particular, when the mixture is made under an inert atmosphere.

In a third consideration, the stability of the mixture is affected by how the polydiorganosiloxane polyamide-containing component is mixed with the organic polymer. Polydiorganosiloxanes are generally immiscible with most other polymeric materials. However, the inventors have found that a wide variety of polymers can be mixed with a polydiorganosiloxane polyamide-containing component when both are in the molten state. Care must be taken that the conditions needed to soften one component does not degrade the other. Preferably, the mixing temperature should be at a temperature above the mixing and conveying temperature of the mixture and below the degradation temperature of the polydiorganosiloxane polyamide-containing component. The polydiorganosiloxane polyoxamide copolymer can usually be subjected to elevated temperatures up to 250° C. or higher without apparent degradation.

Any vessel in which the components can be adequately heated and mixed in the molten state is suitable for making mixtures as disclosed herein.

In a fourth consideration, the processing steps influence the morphology of an article made with the mixtures as disclosed herein. The mixtures generally have at least two domains, one discontinuous and the other continuous, because of the general immiscibility of the polydiorganosiloxane polyamide-containing component with the organic polymer. The component comprising the minor phase typically forms discontinuous domains that range in shape from spheroidal to ellipsoidal to ribbon-like to fibrous. The component comprising the major phase typically forms the continuous domain that surrounds the discontinuous domains. The discontinuous domains of the mixture generally elongate if the mixture is subjected to sufficient shear or extensional forces as the mixture is formed into an article, such as a film or coating. The discontinuous domains generally remain elongated if at least one of the components has a sufficient viscosity at use temperature to prevent the elongated domain from relaxing into a sphere when the mixture is no longer under extensional or shear forces. The elongated morphology is usually stable until the mixture is reheated above the softening point of the components.

While both a solvent based process and a solventless process for making the mixtures as disclosed herein can be used, there may be some situations where a combination of the two is preferred. In the latter case, a polydiorganosiloxane polyamide-containing component could be made by the solvent based process and subsequently dried and melt mixed with the organic polymer.

Types of Articles

Polymers and compositions of the present invention, depending on specific formulation, can be used to make a variety of articles that can be used, for example, as release films, optical films, diffuse optical articles, process aids, optical PSAs, pressure-sensitive adhesive tapes, pressure-sensitive adhesive transfer tapes, pressure-sensitive adhesive medical tapes, including for example transdermal drug delivering devices, rubber-toughened articles, and pressure-sensitive adhesive coatings directly onto desired articles.

Polymers and compositions as disclosed herein can be cast from solvents as film, molded or embossed in various shapes, or extruded into films. They can be formed into various articles, for example, one that includes a layer containing the polymer or composition and one or more optional substrates. For example, the polymer or composition can be in a layer adjacent to a first substrate or positioned between a first substrate and a second substrate. That is, the article can be arranged in the following order: a first substrate, a layer containing the polymer or composition, and a second substrate. As used herein, the term "adjacent" refers to a first layer that contacts a second layer or that is positioned in proximity to the second layer but separated from the second layer by one or more additional layers.

Pressure-sensitive adhesive articles are made by applying the pressure-sensitive adhesive by well known hot melt or solvent coating process. Any suitable substrates that can by used, including, but not limited to, for example, cloth and fiber-glass cloth, metallized films and foils, polymeric films, nonwovens, paper and polymer coated paper, and foam backings. Polymer films include, but are not limited by, polyolefins such as polypropylene, polyethylene, low density polyethylene, linear low density polyethylene and high density polyethylene; polyesters such as polyethylene terephthalate; polycarbonates; cellulose acetates; polyimides such as that available under the trade designation KAPTON. Nonwovens, generally made from randomly oriented fibers, include, but are not limited by, nylon, polypropylene, ethylene-vinyl acetate copolymer, polyurethane, rayon and the like. Foam backings include, but are not limited by acrylic, silicone, polyurethane, polyethylene, neoprene rubber, and polypropylene, and may be filled or unfilled. Backings that are layered, such as polyethylene-aluminum membrane composites, are also suitable.

In the case of pressure-sensitive tapes, these materials are typically applied by first making a tape construction which comprises a layer of the pressure-sensitive adhesive material coated on a backing. The exposed surface of the pressure-sensitive adhesive coating may be subsequently applied to a surface from which it could be released later or directly to the desired substrate.

Some pressure-sensitive adhesive articles use release liners, i.e., transfer tapes that can be made by coating the composition between two liners both of which are coated with a release coating. The release liners typically comprise polymeric material such as polyester, polyethylene, polyolefin and the like, or release coated paper or polyethylene coated paper. Preferably, each release liner is first coated or primed with a release material for the adhesive materials utilized in the invention. When the composition contains a significant amount of a tackified polydiorganosiloxane polyamide-containing component, useful release liners include those that are suitable for use with silicone adhesives. One example is the polyfluoropolyether coated liner described in European Patent Publication No. 433070. Other useful release liner release coating compositions are described in European Patent Publication No. 378420, U.S. Pat. No. 4,889,753, and European Patent Publication No. 311262. Commercially available liners and compositions include that available under the trade designation SYL-OFF Q2-7785 fluorosilicone release coating from Dow Corning Corp., Midland, Mich., X-70-029NS fluorosilicone release coatings available from Shin-Etsu Silicones of America, Inc., Torrance, Calif.; that available under the trade designation S TAKE-OFF 2402 fluorosilicone release liner from Release International, Bedford Park, Ill.; and the like.

Compositions of the present invention are also useful in medical applications including transdermal drug delivery devices. Transdermal drug delivery devices are designed to deliver a therapeutically effective amount of drug through or to the skin of a patient. Transdermal drug delivery provides significant advantages; unlike injection, it is noninvasive; unlike oral administration, it avoids hepatic first pass metabolism, it minimizes gastrointestinal effects, and it provides stable blood levels.

Compositions of the present invention may also be used in pressure-sensitive adhesives that readily attach to prepared and unprepared surfaces, especially metals, polyolefin and fluorine containing polymeric films, providing a highly conformable, continuous interfacial silicone coating that prevents ingress of environmental contaminants including those that corrosively attack unprotected surfaces. A pressure sensitive adhesive patch typically consists of a protective polydiorganosiloxane polyamide-containing pressure sensitive adhesive composition and optionally a barrier or edge adhesive, layers of conformable barrier or backing materials, or combinations of these materials. For some applications it is preferable that the backing does not shield electric field lines, making an open structure backing more preferable to solid films of, for example, polyethylene or PVC. A tapered or profiled adhesive layer to better match surface topology may be preferred when patching some surfaces.

Compositions of the present invention may also be used as pressure-sensitive adhesives or hot melt adhesives for heat shrink tubes. These constructions provide a single article that can withstand the high temperatures experienced during the heat shrink operation and provide an environmental seal after cooling. The rheology, heat stability, tack, and clarity of these materials make them especially suitable for this application.

Compositions of the invention can also be coated onto a differential release liner; i.e., a release liner having a first release coating on one side of the liner and a second release coating coated on the opposite side. The two release coatings preferably have different release values. For example, one release coating may have a release value of 5 grams/cm (that is, 5 grams of force is needed to remove a strip of material 1 cm wide from the coating) while the second release coating may have a release value of 15 grams/cm. The material can be coated over the release liner coating having the higher release value. The resulting tape can be wound into a roll. As the tape is unwound, the pressure-sensitive adhesive adheres to the release coating with the higher release value. After the tape is applied to a substrate, the release liner can be removed to expose an adhesive surface for further use.

Hot melt adhesives are compositions that can be used to bond nonadhering surfaces together into a composite. During application to a substrate, hot melt adhesives should be sufficiently fluid to wet the surface completely and leave no voids, even if the surface is rough. Consequently, the adhesive must be low in viscosity at the time of application. However, the bonding adhesive generally sets into a solid to develop sufficient cohesive strength to remain adhered to the substrate under stressful conditions.

For hot melt adhesives, the transition from fluid to solid may be accomplished in several ways. First, the hot melt adhesive may be a thermoplastic that softens and melts when heated and becomes hard again when cooled. Such heating results in sufficiently high fluidity to achieve successful wetting. Alternatively, the hot melt adhesive may be dissolved in a solvent or carrier that lowers the viscosity of the adhesive sufficiently to permit satisfactory wetting and raises the adhesive viscosity when the solvent or carrier is removed. Such an adhesive can be heat activated, if necessary.

Compositions of the present invention can be formed into unsupported films, which can be used, for example, as release articles, adhesive transfer tapes, optical adhesives, hot melt adhesives, optical articles, diffusers, non-woven webs, water repellant films, rubber toughened plastics, anti-graffiti films, casting liners, pressure sensitive adhesives, vibration dampers, acoustic dampers, medical backings, tape backings, medical articles, and sealants.

Compositions of the present invention can be incorporated into one or more layers of a multilayer film, which can be used, for example, for the uses described herein above for unsupported films. In addition, the multilayer films can be used, for example, as reflective polarizers, infra-red radiation reflectors, diffusers, optical filters, pressure sensitive adhesives, vibration dampers, acoustic dampers, reflectors, and permeable films.

Compositions of the present invention can be used in melt process aids, which can be used, for example, for surface modification, slip aids, compatibiliziers, refractive index modifiers, impact modifiers, optics modifiers, rheology modifiers, permeability modification, water repellency, fiber treatment to impart a perfect smoothness, lubricity, reduced tackiness, and pleasant tactile sensations.

The following exemplary embodiments are provided by the present Disclosure:

Embodiment 1

A copolymer comprising: at least one repeat unit of Formula I-a:

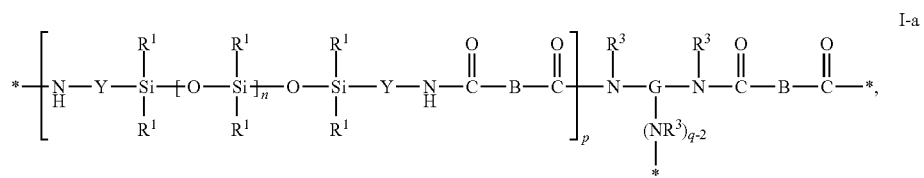

and at least one repeat unit of Formula VI-a:

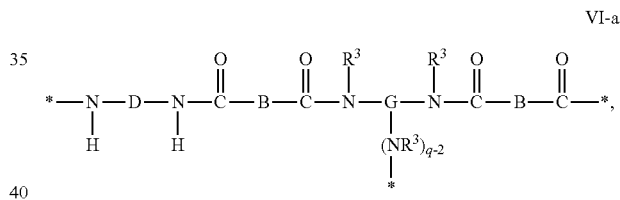

wherein: each $R^1$ is independently an alkyl, haloalkyl, aralkyl, alkenyl, aryl, or aryl substituted with an alkyl, alkoxy, or halo; G is a residue having a valence of q; $R^3$ is hydrogen or alkyl or $R^3$ taken together with G and to the nitrogen to which they are both attached form a heterocyclic group; each Y is independently an alkylene, aralkylene, or a combination thereof; each B is independently a covalent bond, an alkylene of 4-20 carbons, an aralkylene, an arylene, or a combination thereof; D is an organic soft segment residue; n is independently an integer of 0 to 1500; p is an integer of 1 to 10; and q is an integer greater than or equal to 2.

Embodiment 2

The copolymer of embodiment 1, wherein the copolymer comprises: at least one repeat unit of Formula I-b:

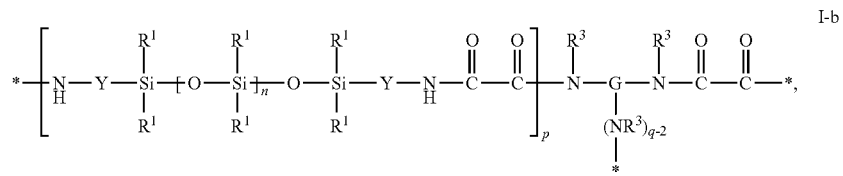

and at least one repeat unit of Formula VI-b:

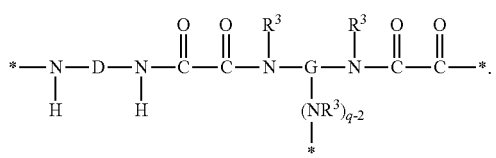

Embodiment 3

The copolymer of embodiment 1 or 2 wherein D comprises a polyether residue.

Embodiment 4

The copolymer of any of embodiments 1 to 3 wherein D comprises a polyoxypropylene residue.

Embodiment 5

The copolymer of embodiment 4 wherein the polyoxypropylene residue has an average molecular weight of from 450 to 8000.

Embodiment 6

The copolymer of any of embodiments 1 to 5, wherein each $R^1$ is methyl.

Embodiment 7

The copolymer of any of embodiments 1 to 5, wherein at least 50 percent of the $R^1$ groups are methyl.

Embodiment 8

The copolymer of any of embodiments 1 to 7, wherein each Y is an alkylene having 1 to 10 carbon atoms, phenylene bonded to an alkylene having 1 to 10 carbon atoms, or phenylene bonded to a first alkylene having 1 to 10 carbon atoms and to a second alkylene having 1 to 10 carbon atoms.

Embodiment 9

The copolymer of any of embodiments 1 to 8, wherein Y is an alkylene having 1 to 4 carbon atoms.

Embodiment 10

The copolymer of any of embodiments 1 to 9, wherein the copolymer has a first repeat unit where p is equal to 1 and a second repeat unit where p is at least 2.

Embodiment 11

The copolymer of any of embodiments 1-10, wherein n is at least 40.

Embodiment 12

The copolymer of any of embodiments 1-11, wherein $R^3$ is hydrogen.

Embodiment 13

A method of making a copolymer having at least one repeat unit of Formula I-a and at least one repeat unit of Formula VI-a, the method comprising mixing together under reaction conditions: a) a precursor of Formula II-a:

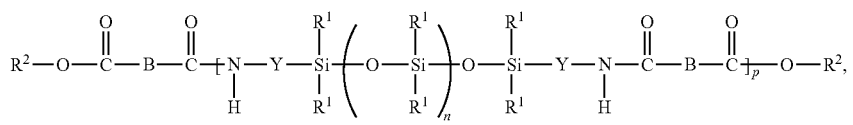

b) a precursor of Formula VII-a:

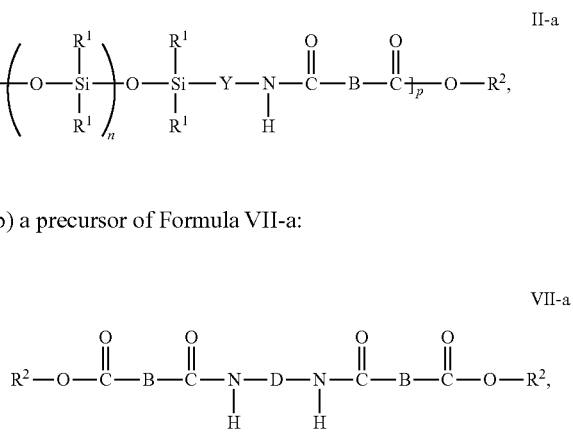

and c) one or more amine compounds having on average a formula $G(NHR^3)_r$, wherein: each $R^1$ is independently an alkyl, haloalkyl, aralkyl, alkenyl, aryl, or aryl substituted with an alkyl, alkoxy, or halo; each $R^2$ is independently an alkyl, haloalkyl, aryl, or aryl substituted with an alkyl, alkoxy, halo, or alkoxycarbonyl; G is a residue unit equal to the formula $G(NHR^3)_r$ minus the r —$NHR^3$ groups; $R^3$ is hydrogen or alkyl or $R^3$ taken together with G and with the nitrogen to which they are both attached forms a heterocyclic group; each Y is independently an alkylene, aralkylene, or a combination thereof; each B is independently a covalent bond, an alkylene of 4-20 carbons, an aralkylene, an arylene, or a combination thereof; D is an organic soft segment residue; n is independently an integer of 0 to 1500; p is an integer of 1 to 10; and r is a number greater than or equal to 2.

Embodiment 14

The method of embodiment 13, where $R^3$ is hydrogen.

Embodiment 15

The method of embodiment 13 or 14, wherein the method further comprises removing a reaction by-product of formula $R^2OH$ from the copolymer.

Embodiment 16

The method of any of embodiments 13 to 15, wherein $R^1$ is methyl and $R^3$ is hydrogen.

Embodiment 17

The method of any of embodiments 13 to 16, wherein the mixing of the precursors and the one or more amine compounds is a batch process, a semi-batch process, or a continuous process.

Embodiment 18

A method of making a copolymer having at least one repeat unit of Formula I-b and at least one repeat unit of Formula VI-b, the method comprising mixing together under reaction conditions: a) a precursor of Formula II-b:

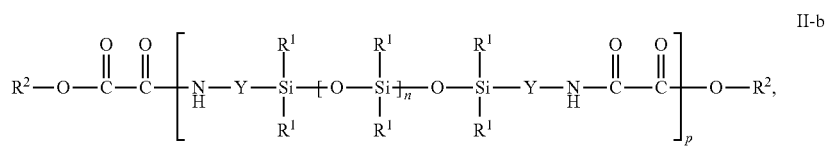

b) a precursor of Formula VII-b:

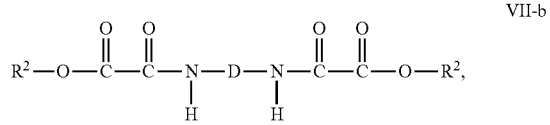

and c) one or more amine compounds having on average a formula $G(NHR^3)_r$, wherein: each $R^1$ is independently an alkyl, haloalkyl, aralkyl, alkenyl, aryl, or aryl substituted with an alkyl, alkoxy, or halo; each $R^2$ is independently an alkyl, haloalkyl, aryl, or aryl substituted with an alkyl, alkoxy, halo, or alkoxycarbonyl; G is a residue unit equal to the formula $G(NHR^3)_r$ minus the r —$NHR^3$ groups; $R^3$ is hydrogen or alkyl or $R^3$ taken together with G and with the nitrogen to which they are both attached forms a heterocyclic group; each Y is independently an alkylene, aralkylene, or a combination thereof; D is an organic soft segment residue; n is independently an integer of 0 to 1500; p is an integer of 1 to 10; and r is a number greater than or equal to 2.

Embodiment 19

The method of embodiment 18, wherein the precursor of Formula II-b is prepared by reacting a polydiorganosiloxane diamine of Formula III

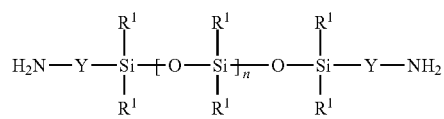

with a molar excess of an oxalate of Formula IV

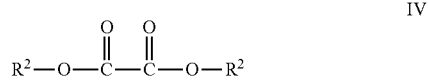

wherein $R^2$ is an alkyl, haloalkyl, aryl, or aryl substituted with an alkyl, alkoxy, halo, or alkoxycarbonyl.

Embodiment 20

The method of embodiment 19, wherein the excess oxalate is removed after reaction with the polydiorganosiloxane diamine.

Embodiment 21

A method of making a copolymer having at least one repeat unit of Formula I-a and at least one repeat unit of Formula VI-a, the method comprising mixing together under reaction conditions: a) a precursor of Formula VIII-a:

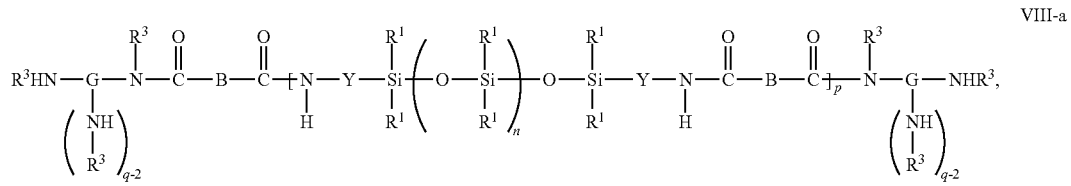

and b) a precursor of Formula VII-a:

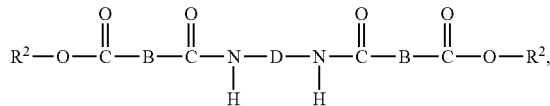

wherein: each $R^1$ is independently an alkyl, haloalkyl, aralkyl, alkenyl, aryl, or aryl substituted with an alkyl, alkoxy, or halo; each $R^2$ is independently an alkyl, haloalkyl, aryl, or aryl substituted with an alkyl, alkoxy, halo, or alkoxycarbonyl; G is a residue unit equal to the formula $G(NHR^3)_q$ minus the q —$NHR^3$ groups; $R^3$ is hydrogen or alkyl or $R^3$ taken together with G and with the nitrogen to which they are both attached forms a heterocyclic group; each Y is independently an alkylene, aralkylene, or a combination thereof; each B is independently a covalent bond, an alkylene of 4-20 carbons, an aralkylene, an arylene, or a combination thereof; D is an organic soft segment residue; n is independently an integer of 0 to 1500; p is an integer of 1 to 10; and q is an integer greater than or equal to 2.

Embodiment 22

The method of embodiment 21, where $R^3$ is hydrogen.

Embodiment 23

The method of embodiment 21 or 22, wherein the method further comprises removing a reaction by-product of formula $R^2OH$ from the copolymer.

Embodiment 24

The method of any of embodiments 21 to 23, wherein $R^1$ is methyl and $R^3$ is hydrogen.

Embodiment 25

The method of any of embodiments 21 to 24, wherein the mixing of the precursors is a batch process, a semi-batch process, or a continuous process.

Embodiment 26

A method of making a copolymer having at least one repeat unit of Formula I-b and at least one repeat unit of Formula VI-b, the method comprising mixing together under reaction conditions: a) a precursor of Formula VIII-b:

and b) a precursor of Formula VII-b:

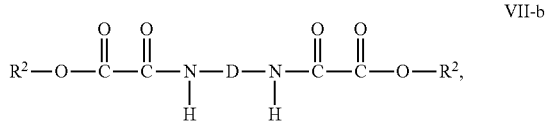

wherein: each $R^1$ is independently an alkyl, haloalkyl, aralkyl, alkenyl, aryl, or aryl substituted with an alkyl, alkoxy, or halo; each $R^2$ is independently an alkyl, haloalkyl, aryl, or aryl substituted with an alkyl, alkoxy, halo, or alkoxycarbonyl; G is a residue unit equal to the formula $G(NHR^3)_q$ minus the q —$NHR^3$ groups; $R^3$ is hydrogen or alkyl or $R^3$ taken together with G and with the nitrogen to which they are both attached forms a heterocyclic group; each Y is independently an alkylene, aralkylene, or a combination thereof; D is an organic soft segment residue; n is independently an integer of 0 to 1500; p is an integer of 1 to 10; and q is an integer greater than or equal to 2.

Embodiment 27

An article comprising a copolymer according to any of embodiments 1 to 12.

Embodiment 28

The article of embodiment 27 further comprising a substrate, wherein the copolymer is in a layer adjacent to the substrate.

Embodiment 29

The article of embodiment 27 further comprising a first substrate and a second substrate, wherein the copolymer is in a layer positioned between the first substrate and the second substrate.

Embodiment 30

A composition comprising a copolymer according to any of embodiments 1-12.

Embodiment 31

The composition of embodiment 30 further comprising a polymeric material different than the copolymer.

Embodiment 32

The composition of embodiment 30 or 31 further comprising a tackifying material.

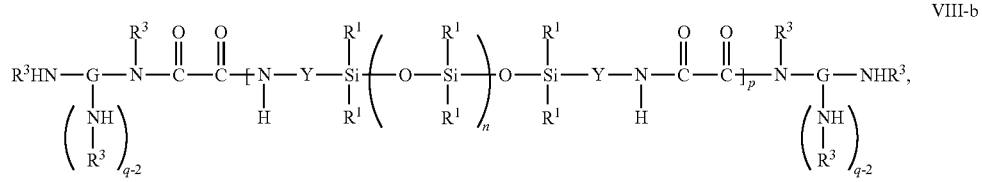

Embodiment 33

The composition of embodiment 32 wherein the tackifying material is a silicate resin or an organic tackifier.

Embodiment 34

The composition of any of embodiments 30 to 33 wherein the composition is an adhesive.

Embodiment 35

The composition of any of embodiments 30 to 34 further comprising one or more additives.

Embodiment 36

A composite film comprising: a first film comprising a light transmissive material; and a second film contiguous to said first film, the second film comprising a copolymer according to any of embodiments 1 to 12.

Embodiment 37

A film comprising: a first layer comprising a first polymeric material having a first index of refraction; and a second layer contiguous to the first layer, the second layer having a second index of refraction and comprising a copolymer according to any of embodiments 1 to 12.

Embodiment 38

The film of embodiment 37 further comprising a third layer contiguous with either the first layer or the second layer, the third layer comprising a third material.

Embodiment 39

The film of embodiment 38 wherein the third layer is disposed between the first layer and the second layer.

The foregoing describes the invention in terms of embodiments foreseen by the inventor for which an enabling description was available, notwithstanding that insubstantial modifications of the invention, not presently foreseen, may nonetheless represent equivalents thereto.

EXAMPLES

These examples are merely for illustrative purposes only and are not meant to be limiting on the scope of the appended claims. All parts, percentages, ratios, and the like in the examples are by weight, unless noted otherwise. Solvents and other reagents used were obtained from Sigma-Aldrich Chemical Company; Milwaukee, Wis. unless otherwise noted.

Table of Abbreviations

| Abbreviation or Trade Designation | Description |
|---|---|
| 5K PDMS diamine | A polydimethylsiloxane diamine with an average molecular weight of 5,000 g/mole that was prepared as described in U.S. Pat. No. 5,214,119 (Leir et al.). |
| THF | Tetrahydrofuran |
| DEO | Diethyl oxalate |

-continued

Table of Abbreviations

| Abbreviation or Trade Designation | Description |
|---|---|
| XTJ-576 | JEFFAMINE D-2000 (i.e., polyoxypropylene diamine having an average molecular weight of 2,000 g/mole), Huntsman, The Woodlands, TX |

Titration Method to Determine Equivalent Weight 10 grams (precisely weighed) of the precursor compounds were added to a jar. Approximately 50 grams THF solvent (not precisely weighed) was added. The contents were mixed using a magnetic stir bar mix until the mixture was homogeneous. The theoretical equivalent weight of precursor was calculated and then an amount of N-hexylamine (precisely weighed) in the range of 3 to 4 times this number of equivalents was added. The reaction mixture was stirred for a minimum of 4 hours. Bromophenol blue (10-20 drops) was added and the contents were mixed until homogeneous. The mixture was titrated to a yellow endpoint with 1.0N (or 0.1N) hydrochloric acid. The number of equivalents of precursor was equal to the number of equivalents of N-hexylamine added to the sample minus the number of equivalents of hydrochloric acid added during titration. The equivalent weight (grams/equivalent) was equal to the sample weight of the precursor divided by the number of equivalents of the precursor.

Preparative Example 1

In a 2 liter, 3-neck resin flask equipped with a mechanical stirrer, heating mantle, nitrogen inlet tube (with stopcock), and an outlet tube was placed diethyl oxalate (145.00 grams). The flask was purged with nitrogen for 15 minutes and, with vigorous stirring, Huntsman XTJ-576 (500.00 grams, MW=2,018) was added over a period of one minute. This reaction mixture was stirred for approximately one hour at room temperature. The reaction flask was fitted with a distillation adaptor and receiver. The reaction mixture was heated to 120° C. under vacuum (1 Torr) for 2 hours, until no further distillate was able to be collected. The reaction mixture was cooled to room temperature to provide the oxamido ester terminated polypropylene oxide product. The ester equivalent weight was determined by titration (eq. wt.=1,191 grams/eq.).

Preparative Example 2

Diethyl oxalate (241.10 grams) was placed in a 3 liter, 3-neck resin flask equipped with a mechanical stirrer, heating mantle, nitrogen inlet tube (with stopcock), and an outlet tube. The flask was purged with nitrogen for 15 minutes and 5 k PDMS diamine (a polydimethylsiloxane diamine with an average molecular weight of 5,000 g/mole that was prepared as described in U.S. Pat. No. 5,214,119 (Leir et al.) (2,028.40 grams, MW=4,918) was added slowly with stirring. After 8 hours at room temperature, the reaction flask was fitted with a distillation adaptor and receiver, the contents stirred and heated to 150° C. under vacuum (1 Torr) for 4 hours, until no further distillate was able to be collected. The remaining liquid was cooled to room temperature to provide 2,573 grams of oxamido ester terminated product. Gas chromatographic analysis of the clear, mobile liquid showed that no detectable level of diethyl oxalate remained. Molecular weight was determined by $^1$H NMR (MW=5,477 grams/mole) and titration (Equivalent weights of 2,547 grams/mole and 2,550 grams/mole).

Preparative Example 3

Ethylene diamine (63.00 grams) was placed in a 3 liter, 3-neck resin flask equipped with a mechanical stirrer, heating mantle, nitrogen inlet tube (with stopcock), and an outlet tube. The flask was purged with nitrogen for 15 minutes and Preparative Example 2, Silicone Polyoxamide (63 grams, MW=5,100) was added slowly with stirring. After 45 minutes at room temperature, the reaction flask was fitted with a distillation adaptor and receiver, the contents stirred and heated to 150° C. under vacuum (1 Torr) for 4 hours, until no further distillate was able to be collected. The remaining waxy solid was cooled to room temperature to provide 2,573 grams of the amine-terminated oxamide polydimethylsiloxane product. Molecular weight was determined by amine titration with bromophenol blue indicator in a THF solution (Equivalent weight of 2,176 grams/mole).

Example 1

This is an example illustrating that a non-silicone soft segment can be introduced into a polymer chain using an ethoxyamide end capped non-silicone prepolymer and a PDMS having the same endgroup. An organic diamine can be used to connect the polymers to form the oxamide links.

To a round bottom flask filled with 119.20 grams of THF, was charged 9.34 grams of polypropyleneoxide diamine (Huntsman XTJ-576, 1009 eq/wt) that was previously capped with diethyl oxalate prepared in a manner similar to that described in Preparative Example 1. Next 20.00 grams of a diethyl oxalate capped PDMS diamine prepared in a manner similar to that described in Preparative Example 2 (2550 eq/wt) was added and allowed to mix. Next 0.476 grams of ethylene diamine was added to the round bottom flask and the reaction was mixed and held at 22° C. for 16 hours. The THF was allowed to evaporate from the formed polymer after pouring to a glass Petri dish. The dry polymer was a clear colorless tough elastomer.

Example 2

This is an example illustrating that a non-silicone soft segment can be introduced into a polymer chain using an ethoxyamide end capped non-silicone prepolymer and a PDMS having the same endgroup. An organic diamine can be used to connect the polymers to form the oxamide links.

To a round bottom flask filled with 24.70 grams of THF, was charged 4.67 grams of polypropyleneoxide diamine (Huntsman XTJ-576, 1009 eq/wt) that was previously capped with diethyl oxalate prepared in a manner similar to that described in Preparative Example 1. Next 10.00 grams of a diethyl oxalate capped PDMS diamine prepared in a manner similar to that described in Preparative Example 2, (2550 eq/wt) was added and allowed to mix. Next 0.5395 grams of m-xylylene diamine was added to the round bottom flask and the reaction was mixed and held at 22° C. for 16 hours. The THF was allowed to evaporate from the formed polymer after pouring to a glass Petri dish. The dry polymer was a clear colorless tough elastomer.

Example 3

This is an example illustrating that a non-silicone soft segment can be introduced into a polymer chain using an ethoxyamide end capped non-silicone prepolymer and a PDMS having amine termination after the oxaminde bond was created on the PDMS segment. No additional organic diamine need be added.

To a round bottom flask filled with 56.50 grams of THF, was charged 5.00 grams of polypropyleneoxide diamine ((Huntsman XTJ-576, 1009 eq/wt) that was previously capped with diethyl oxalate prepared in a manner similar to that described in Preparative Example 1. Next 9.1350 grams of an amine-terminated oxamide polydimethylsiloxane product prepared in a manner similar to that described in Preparative Example 3 was added and allowed to mix while holding at 22° C. for 16 hours. The THF was allowed to evaporate from the formed polymer after pouring to a glass Petri dish. The dry polymer was a clear colorless tough elastomer.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

We claim:
1. A medical article comprising:
   a copolymer comprising:
      at least one repeat unit of Formula I-a:

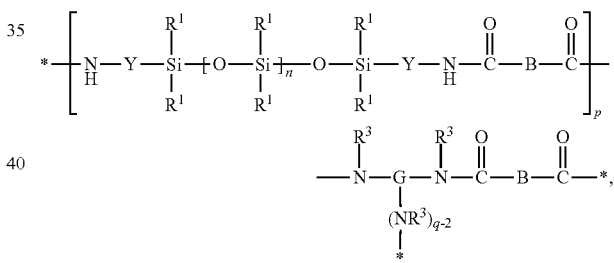

and
at least one repeat unit of Formula VI-a:

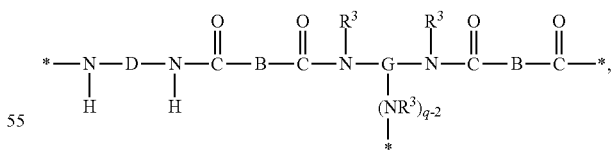

wherein:
   each $R^1$ is independently an alkyl, haloalkyl, aralkyl, alkenyl, aryl, or aryl substituted with an alkyl, alkoxy, or halo;
   G is a residue having a valence of q;
   $R^3$ is hydrogen or alkyl or $R^3$ taken together with G and to the nitrogen to which they are both attached form a heterocyclic group;
   each Y is independently an alkylene, aralkylene, or a combination thereof;

each B is independently a covalent bond, an alkylene of 4-20 carbons, an aralkylene, an arylene, or a combination thereof;
D is an organic soft segment residue;
n is independently an integer of 0 to 1500;
p is an integer of 1 to 10; and
q is an integer greater than 2.

2. The medical article of claim 1, wherein the medical article comprises a sealant.

3. The medical article of claim 1, wherein the medical article further comprises a medical backing.

4. The medical article of claim 1, wherein the copolymer comprises:
at least one repeat unit of Formula I-b:

$$\left[ \text{N(H)}-Y-\underset{R^1}{\underset{|}{\overset{R^1}{\overset{|}{Si}}}}-\left(O-\underset{R^1}{\underset{|}{\overset{R^1}{\overset{|}{Si}}}}\right)_n-O-\underset{R^1}{\underset{|}{\overset{R^1}{\overset{|}{Si}}}}-Y-\text{N(H)}-\overset{O}{\overset{\|}{C}}-\overset{O}{\overset{\|}{C}}-\underset{(NR^3)_{q-2}}{\underset{|}{\overset{R^3}{\overset{|}{N}}}}-G-\underset{*}{\underset{|}{\overset{R^3}{\overset{|}{N}}}}-\overset{O}{\overset{\|}{C}}-\overset{O}{\overset{\|}{C}} \right]_p \quad \text{I-b}$$

and
at least one repeat unit of Formula VI-b:

$$*-\text{N(H)}-D-\text{N(H)}-\overset{O}{\overset{\|}{C}}-\overset{O}{\overset{\|}{C}}-\underset{(NR^3)_{q-2}}{\underset{|}{\overset{R^3}{\overset{|}{N}}}}-G-\underset{*}{\underset{|}{\overset{R^3}{\overset{|}{N}}}}-\overset{O}{\overset{\|}{C}}-\overset{O}{\overset{\|}{C}}-* \quad \text{VI-b}$$

5. The medical article of claim 1, wherein D comprises a polyether residue.

6. The medical article of claim 5, wherein D comprises a polyoxypropylene residue.

7. The medical article of claim 6, wherein the polyoxypropylene residue has an average molecular weight of from 450 to 8000.

8. The medical article of claim 1, wherein each $R^1$ is methyl.

9. The medical article of claim 1, wherein at least 50 percent of the $R^1$ groups are methyl.

10. The medical article of claim 1, wherein each Y is an alkylene having 1 to 10 carbon atoms, phenylene bonded to an alkylene having 1 to 10 carbon atoms, or phenylene bonded to a first alkylene having 1 to 10 carbon atoms and to a second alkylene having 1 to 10 carbon atoms.

11. The medical article of claim 1, wherein Y is an alkylene having 1 to 4 carbon atoms.

12. The medical article of claim 1, wherein the copolymer has a first repeat unit where p is equal to 1 and a second repeat unit where p is at least 2.

13. The medical article of claim 1, wherein n is at least 40.

14. A multilayer medical article comprising:
a medical backing; and
a copolymer comprising:
at least one repeat unit of Formula I-a:

$$\left[ \text{N(H)}-Y-\underset{R^1}{\underset{|}{\overset{R^1}{\overset{|}{Si}}}}-\left(O-\underset{R^1}{\underset{|}{\overset{R^1}{\overset{|}{Si}}}}\right)_n-O-\underset{R^1}{\underset{|}{\overset{R^1}{\overset{|}{Si}}}}-Y-\text{N(H)}-\overset{O}{\overset{\|}{C}}-B-\overset{O}{\overset{\|}{C}}-\underset{(NR^3)_{q-2}}{\underset{|}{\overset{R^3}{\overset{|}{N}}}}-G-\underset{*}{\underset{|}{\overset{R^3}{\overset{|}{N}}}}-\overset{O}{\overset{\|}{C}}-B-\overset{O}{\overset{\|}{C}} \right]_p \quad \text{I-a}$$

and
at least one repeat unit of Formula VI-a:

$$*-\text{N(H)}-D-\text{N(H)}-\overset{O}{\overset{\|}{C}}-B-\overset{O}{\overset{\|}{C}}-\underset{(NR^3)_{q-2}}{\underset{|}{\overset{R^3}{\overset{|}{N}}}}-G-\underset{*}{\underset{|}{\overset{R^3}{\overset{|}{N}}}}-\overset{O}{\overset{\|}{C}}-B-\overset{O}{\overset{\|}{C}}-* \quad \text{VI-a}$$

wherein:
each $R^1$ is independently an alkyl, haloalkyl, aralkyl, alkenyl, aryl, or aryl substituted with an alkyl, alkoxy, or halo;
G is a residue having a valence of q;
$R^3$ is hydrogen or alkyl or $R^3$ taken together with G and to the nitrogen to which they are both attached form a heterocyclic group;
each Y is independently an alkylene, aralkylene, or a combination thereof;
each B is independently a covalent bond, an alkylene of 4-20 carbons, an aralkylene, an arylene, or a combination thereof;
D is an organic soft segment residue;
n is independently an integer of 0 to 1500;
p is an integer of 1 to 10; and
q is an integer greater than 2.

15. The multilayer medical article of claim 14, further comprising at least one additional film layer.

16. The multilayer medical article of claim 14, wherein the copolymer comprises:
at least one repeat unit of Formula I-b:

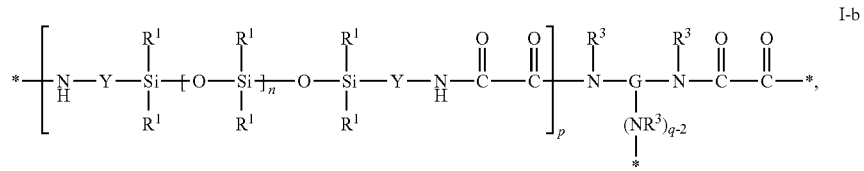

and
at least one repeat unit of Formula VI-b:

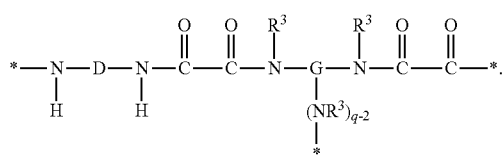

17. The multilayer medical article of claim 14, wherein D comprises a polyoxypropylene residue having an average molecular weight of from 450 to 8000.

18. The multilayer medical article of claim 14, wherein each Y is an alkylene having 1 to 10 carbon atoms, phenylene bonded to an alkylene having 1 to 10 carbon atoms, or phenylene bonded to a first alkylene having 1 to 10 carbon atoms and to a second alkylene having 1 to 10 carbon atoms.

19. The multilayer medical article of claim 14, wherein the copolymer has a first repeat unit where p is equal to 1 and a second repeat unit where p is at least 2.

20. The multilayer medical article of claim 14, wherein n is at least 40.

* * * * *